(12) United States Patent
Cuthbertson et al.

(10) Patent No.: US 8,444,955 B2
(45) Date of Patent: May 21, 2013

(54) RADIOFLUORINATION METHODS

(75) Inventors: Alan Cuthbertson, Oslo (NO); Magne Solbakken, Oslo (NO); Dag Erlend Olberg, Kjeller (NO)

(73) Assignee: GE Healthcare Limited, Buckinghamshire (GB)

( * ) Notice: Subject to any disclaimer, the term of this patent is extended or adjusted under 35 U.S.C. 154(b) by 268 days.

(21) Appl. No.: 12/676,427

(22) PCT Filed: Sep. 9, 2008

(86) PCT No.: PCT/US2008/075684
§ 371 (c)(1),
(2), (4) Date: Mar. 4, 2010

(87) PCT Pub. No.: WO2009/035959
PCT Pub. Date: Mar. 19, 2009

(65) Prior Publication Data
US 2010/0196270 A1    Aug. 5, 2010

Related U.S. Application Data

(60) Provisional application No. 60/971,007, filed on Sep. 10, 2007.

(51) Int. Cl.
*A61K 51/00*    (2006.01)

(52) U.S. Cl.
USPC ............................ 424/1.89; 424/1.69; 514/543

(58) Field of Classification Search
USPC ..................... 424/1.11, 1.69, 1.89; 514/543
See application file for complete search history.

(56) References Cited

FOREIGN PATENT DOCUMENTS

WO    2006/030291    3/2006
WO    2008/083191    7/2008

OTHER PUBLICATIONS

Olberg, et.al. "A Novel Prosthetic Group for Site-Selective Labeling of Peptides for Positron Emission Tomography" Bioconjugate Chemistry 2008, vol. 19, No. 6, Jun. 6, 2008 pp. 1301-1308.
Carrasco, et.al. "Chemoselective Alkylation of N-Alkylaminooxy-Containing Peptides" Organic Letters Aug. 3, 2006, vol. 8, No. 16, pp. 3529-3532.
Bark, et.al. "A Highly Efficient Method for Site-Specific Modification of Unprotected Peptides After Chemical Synthesis" Journal of the American Chemical Sociaety, Wash. DC, vol. 122, No. 15, Apr. 19, 2000, pp. 3567-3573.
PCT/US2008/075684 Int'l Search Report/Written Opinion Dated Nov. 6, 2009.

*Primary Examiner* — Michael G Hartley
*Assistant Examiner* — Jagadishwar Samala

(57) ABSTRACT

The invention relates to conjugates of formula (V) or (VI), their use as radiopharmaceuticals, processes for their preparation, and synthetic intermediates used in such processes.

4 Claims, 5 Drawing Sheets

HPLC chromatogram of $^{18}$F-conjugate of compound 3. Above chromatogram: Left peak unreacted $^{18}$F-synthon, right peak $^{18}$F-synthon-compound 3 conjugate. Lower chromatogram $^{19}$F-synthon-compound 3 reference standard (254nm).

HPLC chromatogram of $^{18}$F-conjugate of compound 6. Above chromatogram: Left peak unreacted $^{18}$F-synthon; right peak $^{18}$F-synthon-compound 6 conjugate. Lower chromatogram: $^{19}$F-synthon-compound 6 reference standard (254nm).

HPLC chromatogram of $^{18}$F-conjugate of compound 7. Above chromatogram: Left peaks unreacted $^{18}$F-synthon; right peak $^{18}$F-synthon-compound 7 conjugate. Lower chromatogram: $^{19}$F-synthon-compound 7 reference standard (254nm).

HPLC chromatogram of 18F-conjugate of compound 8. Above chromatogram: Left peak unreacted 18F-synthon; right peak 18F-synthon-compound 8 conjugate. Lower chromatogram: 19F-synthon-compound 8 reference standard (254nm).

HPLC chromatogram of $^{18}$F-conjugate of compound 11. Above chromatogram: $^{19}$F-synthon-compound 11 reference standard (254nm). Lower chromatogram: Left peak: unreacted $^{18}$F-synthon; right peak $^{18}$F-synthon-compound 11 conjugate.

RADIOFLUORINATION METHODS

This application is a filing under 35 U.S.C. 371 of international application number PCT/US2008/075684, filed Sep. 9, 2008, which claims priority to U.S. application No. 60/971,007 filed Sep. 10, 2007, the entire disclosure of which is hereby incorporated by reference.

FIELD OF INVENTION

The present invention relates to diagnostic and radiodiagnostic agents, including biologically active vectors labelled with positron-emitting nuclides. It further relates to methods and reagents for [$^{18}$F]-fluorination of vectors, where a vector is defined as a molecule with an affinity for a specific biological target, and is preferably a peptide. The resultant $^{18}$F-labelled conjugates are useful as radiopharmaceuticals, specifically for use in Positron Emission Tomography (PET).

BACKGROUND OF THE INVENTION

The application of radiolabelled bioactive peptides for diagnostic imaging is gaining importance in nuclear medicine. Biologically active molecules which selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of approximately 110 minutes, is the positron-emitting nuclide of choice for many receptor imaging studies. Therefore, $^{18}$F-labelled bioactive peptides have great clinical potential because of their utility in PET to quantitatively detect and characterise a wide variety of diseases.

One difficulty with $^{18}$F-labelled peptides is that the existing $^{18}$F-labelling agents are time-consuming to prepare. Efficient labelling of peptides and proteins with $^{18}$F is only achieved by using suitable prosthetic groups. Several such prosthetic groups have been proposed in the literature, including N-succinimidyl-4-[$^{18}$F]fluorobenzoate, m-maleimido-N-(p-[$^{18}$F]fluorobenzyl)-benzamide, N-(p-[$^{18}$F]fluorophenyl) maleimide, and 4-[$^{18}$F]fluorophenacylbromide. Almost all of the methodologies currently used today for the labeling of peptides and proteins with $^{18}$F utilize active esters of the fluorine labelled synthon. As peptides and proteins may contain a multitude of functional groups capable of reaction with active esters these current methods are not site-specific. For example a peptide containing three lysine residues has three amine functions all equally reactive towards the labelled synthon. Therefore, there still exists a need for $^{18}$F-labelled prosthetic groups and methodologies, which allow rapid, chemoselective introduction of $^{18}$F, particularly into peptides, under mild conditions to give $^{18}$F-labelled products in high radiochemical yield and purity. Additionally, there is a need for such methodologies which are amenable to automation to facilitate preparation of radiopharmaceuticals in the clinical setting. Although we have previously described the use of aminoxy chemistry in PET labelling strategies (WO03/006491) the compounds of this invention do not react readily aldehydes and ketones but are selective for some halogen-containing compounds. The greater chemical stability of the N-alkylaminoxy moiety provides an advantage over the aminoxy group previously disclosed as side-reactions are minimised and intermediates are more stable which aids successful handling and storage of intermediates.

DETAILED DESCRIPTION OF THE INVENTION

Figure 1:
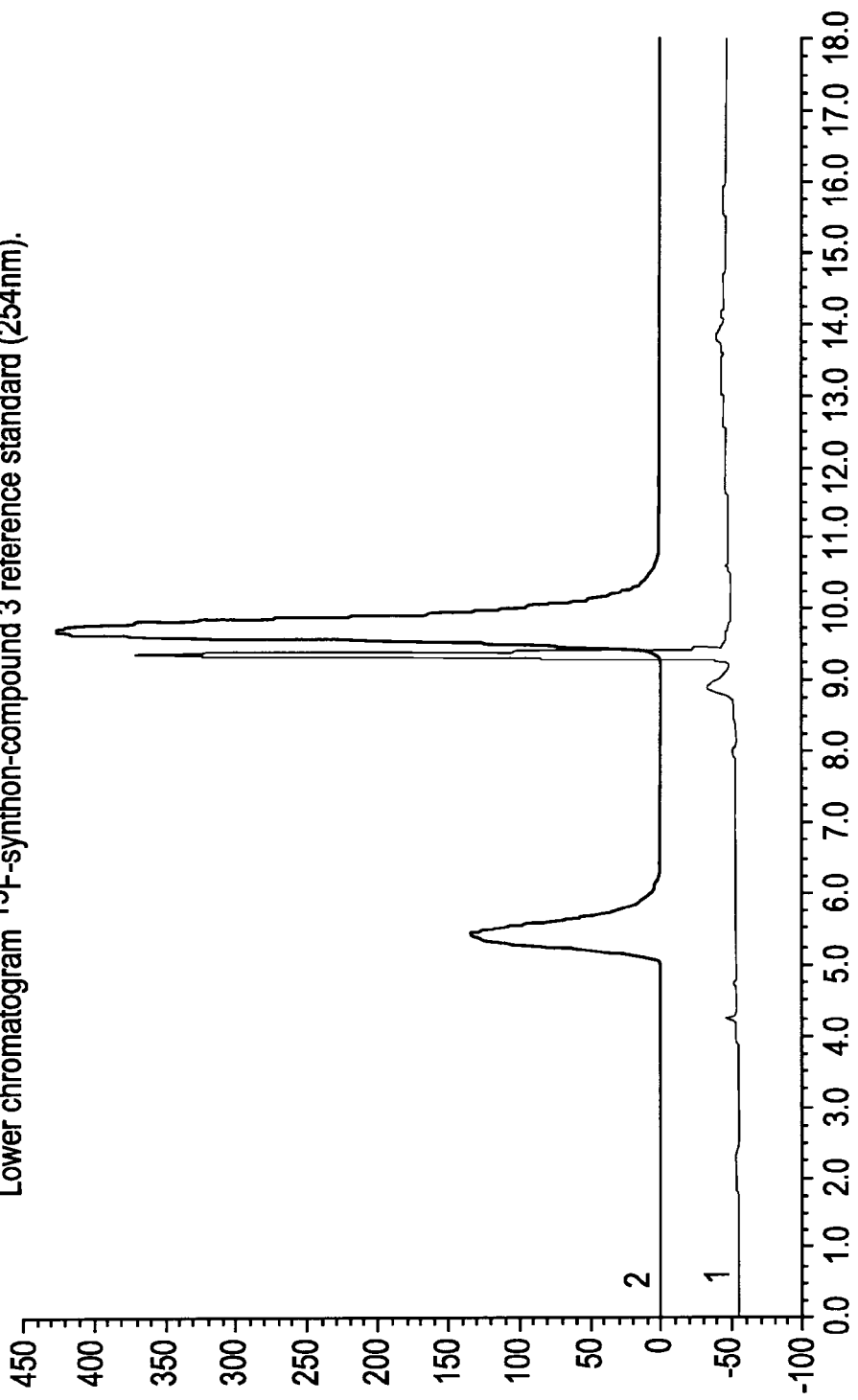
FIG. 1 shows HPLC chromatogram of $^{18}$F-conjugate of compound 3. Above chromatogram: Left peak unreacted $^{18}$F-synthon, right peak $^{18}$F-synthon-compound 3 conjugate. Lower chromatogram $^{19}$F-synthon-compound 3 reference standard (254 nm).

The present invention provides a method for radiofluorination comprising reaction of a compound of formula (I) with a compound of formula (II):

(I)

(II)

or, a compound of formula (III) with a compound of formula (IV)

(III)

(IV)

wherein

R1 is a reactive halogen-containing group such as a haloacetyl, haloallyl or phenacylhalides or is an epoxide ring all groups suitable for participating in alkylation reactions or is a Michael acceptor such as the maleimide group or an acrylic acid or substituted acrylic acid derivative or is a vinylstyrene preferable nitrovinylstyrene or is a vinylsulphonamides or is a vinylsulphone.

R2 is the N-alkyl-aminooxy group which under mild conditions such as aqueous buffer and slightly acidic pH reacts site-specifically with R1 yielding compounds of formula (V).

Wherein R3 of formula (III)=R2 and the R4 of formula (IV)=R1. Ligation of compounds of formula (III) with compounds of formula (IV) yield products of formula (VI

(V)

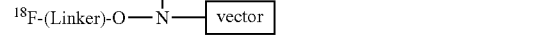

(VI)

wherein in both cases Y is alkyl, preferably Y=—CH3.

Compounds of formula (V) are most preferred and the 18F-Linker component of compounds of formulae (II) preferably comprise compounds of the type shown in formula (VII-XI).

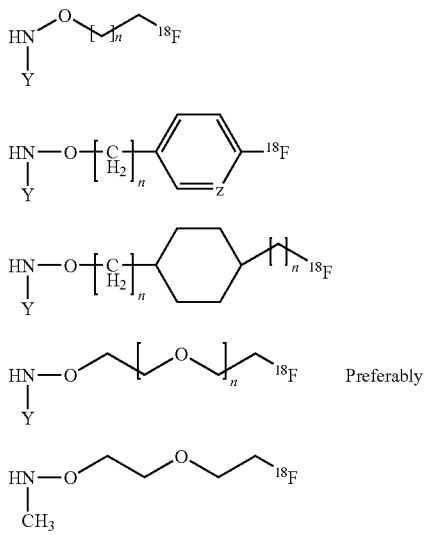

where n= n is an integer of 0 to 20;

Z is O, N or S.

The Linker group in the compounds of formulae (II) may also be chosen to provide optimal in vivo pharmacokinetics, such as favourable excretion characteristics in the resultant conjugate of formula (V). The use of linker groups with different lipophilicities can significantly change the in vivo pharmacokinetics of the peptide to suit the diagnostic need. For example, where it is desirable for a conjugate of formula (V) to be cleared from the body by renal excretion, a hydrophilic linker is used comprising linker components derived from formulas X-XI. Likewise it is desirable for clearance to be by hepatobiliary excretion a hydrophobic linked can be chosen comprising linker components derived from formulas VII-IX.

The present invention provides a more chemoselective approach to radiolabelling where the exact site of introduction of the label is pre-selected during the synthesis of the peptide or vector precursor. The ligation reaction occurring at a pre-determined site in the molecule and gives only a single labeled product. This methodology is therefore chemoselective, and its application is considered generic for labeling a wide range of drug-like molecules, peptides biomolecules such as small proteins.

In a further aspect, the present invention provides a method for radiofluorination comprising reaction of a compound of formula (Ia) with a compound of formula (IIa):

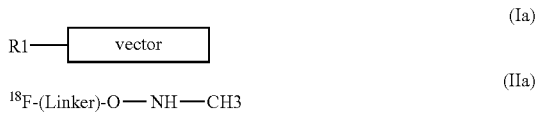

(Ia)

$^{18}$F-(Linker)-O—NH—CH3 (IIa)

or, a compound of formula (IIIa) with a compound of formula (IVa)

(IIIa)

$^{18}$F-(Linker)-R4 (IVa)

wherein R1 and R4 are as defined above for the compounds of formula (I) and (IV) respectively to give a conjugates of formula (Va) or (VIa) respectively:

(Va)

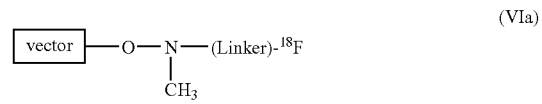

(VIa)

wherein the Linker group is as defined for the compounds above.

The reaction may be effected in a suitable solvent, for example, in an aqueous buffer in the pH range 3 to 11, and at a non-extreme temperature of from 5 to 70° C. but most preferably at ambient temperature.

In a further aspect of this invention R1 is derived from the class of maleimide and vinylstyrene compounds and most preferably represented in the formulas Ib and Ic below:

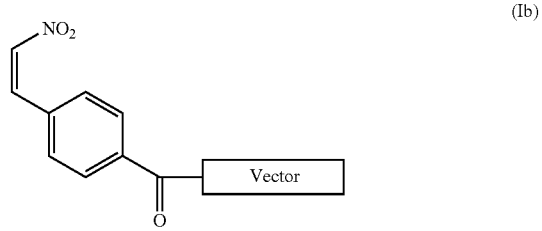

(Ib)

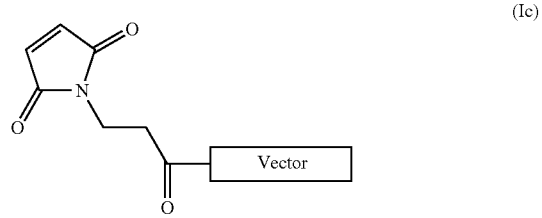

(Ic)

In formulae (I) and (III) and in other aspects of the invention unless specifically stated the vector can be defined as a biological with affinity for a relevant receptor associated with disease process. The biological can be a defined as small molecule drug-like pharmacophore a protein or antibody but is preferably a protein below a molecular weight of 30 kDa and most preferably a peptide of below 100 amino acids. Examples of preferred peptide vectors for labelling using the methods of this invention somatostatin derivatives such as octreotide, bombesin, vasoactive intestinal peptide, chemotactic peptide analogues, α-melanocyte stimulating hormone, neurotensin, Arg-Gly-Asp peptides, human pro-insulin connecting peptide, endothelin, angiotensin and formyl-norleucyl-leucyl-phenylalanyl-norleucyl-tyrosyl-lysine. Preferred peptides for labelling are Arg-Gly-Asp peptide and analogues, such as those described in WO 01/77415 and WO 03/006491. Preferred peptide vectors comprise the fragment of formula (A)

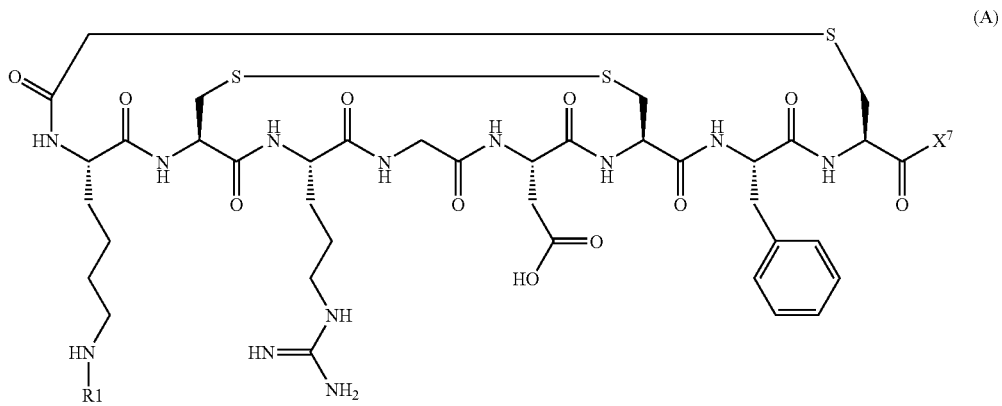
(A)

wherein X⁷ is either —NH₂ or the ethylglycol-containing structure

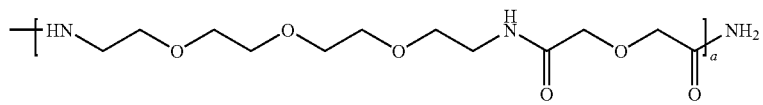

wherein 'a' is an integer of from 1 to 10, but most preferably 'a' is 1.
and R1 is as previously described for formula (I)

As will be appreciated by the skilled person, the methods of the invention may also be used for radiofluorination of other biomolecules such as proteins, hormones, oligonucleotides, and antibody fragments, as well as small drug-like molecules to provide a variety of PET tracers.

Compounds of formula (I) and (III) may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the group R1 and R3 in a compound of formula (I) or (III) may be achieved by reaction of the N or C-terminus of the peptide or with some other functional group contained within the peptide sequence, modification of which does not affect the binding characteristics of the vector. In a preferred example the N-alkylaminoxy-containing group, Y—NH₂—O—, may be directly introduced into the peptide sequence using the amino acids described by Carrasco et al (Biopolymers, Peptide Science, 2006, Vol 84 (4), page 414). The functional groups R1 and R3 are preferably introduced by formation of a stable amide bond formed by reaction of a peptide amine function with an activated acid and introduced either during or following the peptide synthesis. When the precursor is an acid then R1 and R3 can be introduced using in situ activating agents such as 2-(1H-benzotriazole-1-yl)-1,1,3,3-tetramethyluronium hexafluorophosphate (HBTU) or N-[(dimethylamino)-1H-1,2,3-triazolo[4,5-b]pyridin-1-ylmethylene]-N-methylmethanaminium hexafluorophosphate N-oxide (HATU).

Compounds of formula (II) may be prepared from the corresponding precursors of formula (XII):

$$\text{L-linker-O} - \text{N} \overset{Y}{\underset{R5}{\diagdown}} \qquad (XII)$$

wherein L is a leaving group preferably a p-toluenesulphonate, trifluoromethanesulphonate, or methanesulphonate or a halide and Y and Linker are as defined previously and where R5 is a suitable protecting group for protection of the nitrogen atom such as the t-butyloxycarbonyl group and whereby reaction with cyclotron produced aqueous [¹⁸F]-fluoride, suitably pre-activated by evaporation from a base (for example, from tetrabutylammonium or K₂CO₃/Kryptofix-222), in a suitable solvent such as acetonitrile, N,N-dimethylformamide, or dimethyl sulphoxide, typically at elevated temperature, for example 60 to 150° C., suitably 60 to 120° C. or by microwave heating, followed by removal of any N-protecting group using standard methods such as acidolytic treatment.

Compounds of formula (IV) may be prepared from the corresponding precursors of formula (XX):

L-linker-R4 (XX)

or a protected derivative thereof, wherein L is a leaving group preferably a p-toluenesulphonate, trifluoromethanesulphonate, or methanesulphonate or a halide and the Linker and R4 are as defined previously. L is capable of reacting with cyclotron produced aqueous [¹⁸F]-fluoride, suitably pre-activated by evaporation from a base (for example, from tetrabutylammonium or K₂CO₃/Kryptofix-222), in a suitable solvent such as acetonitrile, N,N-dimethylformamide, or dimethyl sulphoxide, typically at elevated temperature, for example 60 to 120° C.

The present invention also provides a radiopharmaceutical composition comprising an effective amount (e.g. an amount effective for use in in vivo PET imaging) of a compound of general formula (V) or (VI), together with one or more pharmaceutically acceptable adjuvants, excipients or diluents.

A preferred embodiment of the invention relates to a compound of general formula (V) or (VI), for medical use and particularly for use in tumour imaging (suitably by PET); wherein the vector is an Arg-Gly-Asp peptide or an analogue thereof, such as those described in WO 01/77415 and WO 03/006491, preferably a peptide comprising the fragment

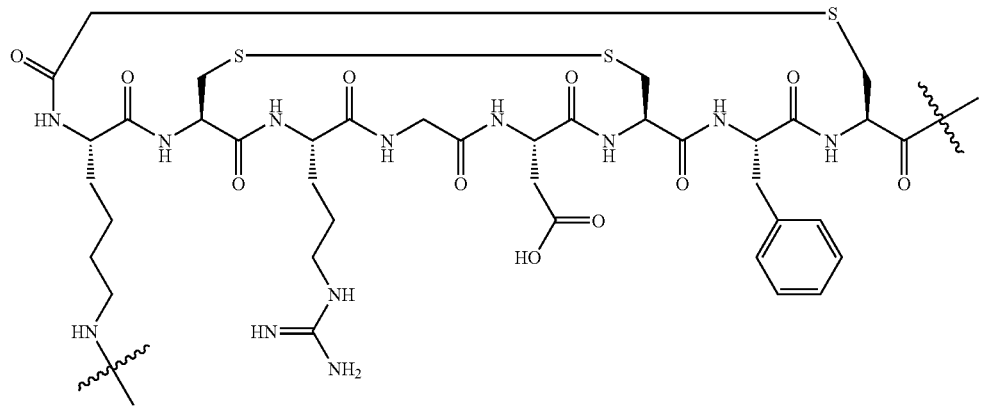

more preferably the peptide of formula (A):

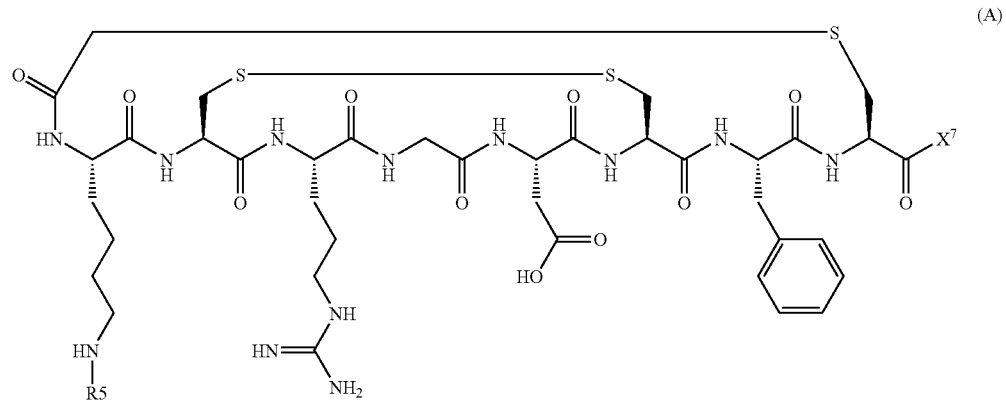

wherein $X^7$ is either —$NH_2$ or

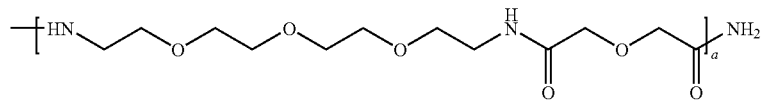

wherein 'a' is an integer of from 1 to 10, preferably a is 1 and where R5 forms an amide bond with the ε-amino of the lysine residue following reaction of the peptide and is defined by R1 but most preferably is illustrated by the structures Id and Ie.

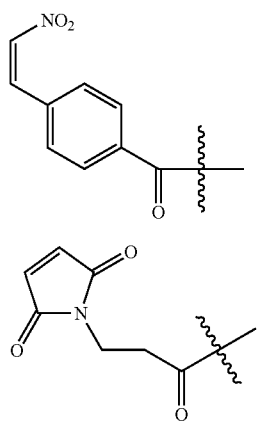

to provide of formula (I) having the structures shown in (If and Ig)

ologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Viewed from a further aspect the invention provides the use of a radiolabelled conjugate of the invention for the manufacture of a radiopharmaceutical for use in a method of in vivo imaging, suitably PET, and preferably for tumour imaging; involving administration of said radiopharmaceutical to a human or animal body and generation of an image of at least part of said body.

Viewed from a still further aspect the invention provides a method of generating an image of a human or animal body involving administering a radiopharmaceutical to said body, e.g. into the vascular system and generating an image of at least a part of said body to which said radiopharmaceutical has distributed using PET, wherein said radiopharmaceutical comprises a radiolabelled conjugate according to the invention.

Viewed from a further aspect the invention provides a method of monitoring the effect of treatment of a human or animal body with a drug to combat a condition associated with cancer, preferably angiogenesis, e.g. a cytotoxic agent, said method comprising administering to said body a radiolabelled conjugate according to the invention and detecting

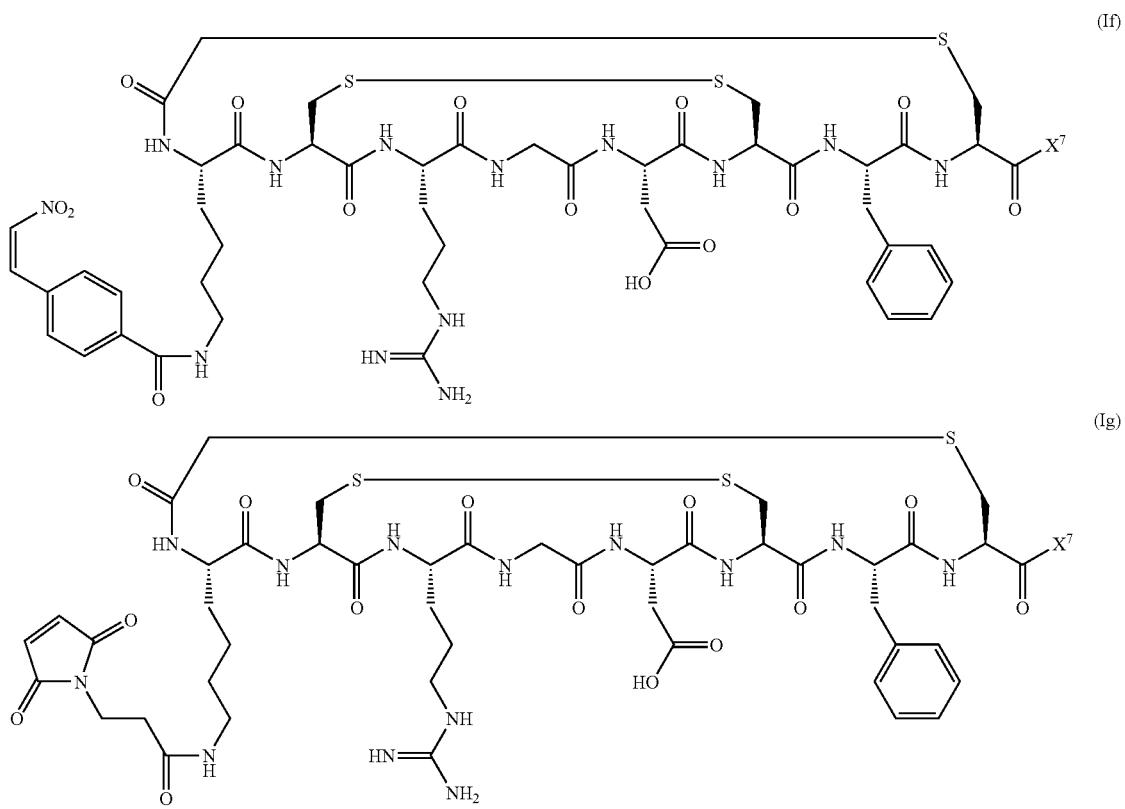

The radiolabelled conjugates of the invention may be administered to patients for PET imaging in amounts sufficient to yield the desired signal, typical radionuclide dosages of 0.01 to 100 mCi, preferably 0.1 to 50 mCi will normally be sufficient per 70 kg bodyweight.

The radiolabelled conjugates according to the invention may therefore be formulated for administration using physithe uptake of said conjugate by cell receptors, preferably endothelial cell receptors and in particular αvβ3 receptors, said administration and detection optionally but preferably being effected repeatedly, e.g. before, during and after treatment with said drug.

In yet another embodiment of the instant invention, there is provided a kit for the preparation of a radiofluorinated tracer comprising a prosthetic group of formula (II) or (IV) and a compound of formula (I) or (III).

According to a further aspect of the invention, there is provided a kit for the preparation of a radiofluorinated tracer comprising a prosthetic group of formula (xx) and a compound of formula (I). According to another aspect of the invention, there is provided a kit for the preparation of a radiofluorinated tracer comprising a prosthetic group of formula ( ) or ( ) and a compound of formula (III).

In use of the kits, the compound of formula ( ) would be converted to the corresponding compound of formula (II) and the compound of formula ( ) or ( ) would be converted to the corresponding compound of formula (IV), respectively, using methods described above. Preferably, the compound of formula (II) and (IV) may be separated from waste reactants by passing the reaction mixture through a Solid Phase Extraction (SPE) cartridge. The SPE cartridge may comprise a graphite pad, $C_{18}$ stationary phase or ion exchange resin. The compound of formula (II) and (IV) would then be added to the compounds of formula (I) and (III) respectively which may suitably be dissolved in aqueous buffer (pH 3-11). After reaction at a non-extreme temperature for 1 to 70 minutes, the labelled peptide may be purified, for example, by SPE and collected.

EXAMPLES

The invention is illustrated by way of examples in which the following abbreviations are used.
HPLC: high performance liquid chromatography
NMR: nuclear magnetic resonance
hr(s): hours(s)
min(s): minutes(s)
THF: tetrahydrofuran
DCM: dichloromethane
DMF: N,N-dimethylformamide
TBAF: tetrabutylammonium fluoride
MeOH: methanol
DMSO: Dimethylsulphoxide
Boc: t-butoxycarbonyl
RT: room temperature
i-Pr$_2$-Net: N,N-Diisopropylethylamine
t-BDPSiCl: tert-butyldiphenylsilyl chloride
NaH: Sodiumhydride
EtOAc: Ethyl acetate
MBq: Mega becquerel
The following mobile phase/gradient systems were used: solvent A: water (0.1%) TFA, solvent B: acetonitrile (0.1% TFA)

Example 1

Preparation of Toluene-4-sulfonic acid 4-(N-Methyl-N-Boc-aminooxy)-butyl ester

Compound 1

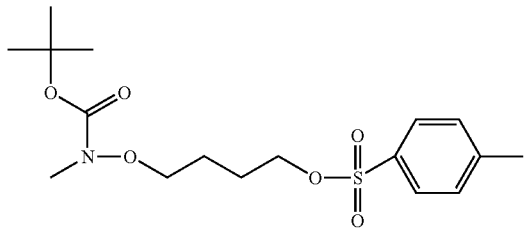

(a) N-Boc-N-methylhydroxylamine

N-methyl-hydroxylamine (4.2 g, 0.05 mol) was dissolved in a 50% aqueous tetrahydrofuran (THF) (20 ml) and cooled on ice while stirring. Potassium carbonate (3.6 g, 0.0275 mol) was added to the ice-cooled solution followed by di-tert-butyl dicarbonate (12 g, 0.055 mol) dissolved in 15 ml THF. The mixture was stirred at 0° C. for 2 hours and at room temperature for 2 hours. The THF was removed under reduced pressure and the residue was dissolved in DCM. The solution was washed two times with water, dried (MgSO$_4$), and concentrated giving a pink low viscous oil of 6.47 g (88%). The product was identified by electrospray mass spectrometry (ESI-MS)(MH$^+$ calculated 147.09; found 147.6). The product was used in without further purification.

(b) (4-bromo-butoxy)-tert-butyl-diphenyl-silane

To a solution of 4-bromo-1-butanol (2.75 g, 18 mmol) in DCM (10 ml) containing i-Pr$_2$-Net (10 ml) was added t-BDP-SiCl (5 ml, 18 mmol) under argon atmosphere. The solution was stirred at room temperature for 2 hours, concentrated in vacuo, and chromatographed (Hexane/ethyl acetate 10:1). Giving a low viscous colour free oil of 4.39 g (62%). Structure confirmed with NMR.

(c) O-[4-(tert-butyl-diphenyl-silanyloxy)-butyl]-N-methyl-N-Boc-hydroxylamine

N-Boc-N-methylhydroxylamine (a) (0.74 g, 5 mmol) was dissolved in 10 ml DMF, treated with NaH (200 mg, 60% dispersion in mineral oil, 4.75 mmol), and stirred for 1 h under an argon atmosphere. The mixture was cooled to 0° C., treated with a solution of 4-bromo-butoxy)-tert-butyl-diphenyl-silane (b) (1.56 g, 4 mmol) in DMF (10 mL) and stirred at 0° C. for an additional 3 hours. The solvents were removed under reduced pressure, and the residue was dissolved in EtOAc (150 mL) and poured into a separatory funnel. The organic layer was washed with 0.1 M NaOH (5×50 mL), H$_2$O (50 ml), 0.1 M KHSO$_4$, and brine (50 ml) and the dried with MgSO$_4$. After removal of the solvent, the residue was chromatographed on silicagel (Hexane:EtOAc 10:1) to yield 0.588 g (24%). The product was identified by electrospray mass spectrometry (ESI-MS)(MH$^+$ calculated 457.26; found 457.8)

(d) 4-(N-methyl-N-Boc-hydroxylamine)-butan-1-ol

TBAF (1.6 mL, 1.586 mmol) was added to O-[4-(tert-butyl-diphenyl-silanyloxy)-butyl]-N-methyl-N-Boc-hydroxylamine (c)(588 mg, 1.22 mmol) dissolved in dry THF 20 mL. The reaction was stirred over night under argon. NH$_4$Cl (saturated) was added to the solution (10 mL×3) and the THF was evaporated. The solution was extracted with DCM, the organic phase was dried (Na$_2$SO$_4$) and evaporated. The residue was chromatographed (Hexane/EtOAc 1:1) on silicagel to give 0.170 g (63%). The product was analyzed by HPLC (column:Phenomenex Luna 3μ C18 (2), 4.6×50 mm, detection: 214 nm, gradient:50%-100% B over 10 min where A=H$_2$O/0.1% TFA and B=acetonitrile/0.1% TFA, flow rate: 2 mL/min, Rt=2.70 min). Further confirmation was carried out by NMR analysis.

(e) Toluene-4-sulfonic acid 4-(N-methyl-N-Boc-hydroxylamine)-butyl ester

To a ice bath cooled stirred solution of 4-(N-methyl-N-Boc-hydroxylamine)-butan-1-ol (d) (170 mg, 0.77 mmol) and triethylamine (161 μL, 1.155 mmol) in dry DCM 10 mL was added toluene-4-sulfonylchloride (190.8 mg, 1.001 mmol) in dry DCM (5 mL) under argon. The ice bath was removed after 15 minutes and the reaction mixture was left at room temperature. After 2 hours new reagents were added (triethylamine (32 µL, 0.23 mmol), toluene-4-sulfonylchloride (29.36 mg, 0.154 mmol). After 24 hours presumed product can be observed on TLC. 30 hours: New reagents were added to the reaction mixture (triethylamine (53 µL, 0.385 mmol), toluene-4-sulfonylchloride (73.5 mg, 0.385 mmol) and left over night. The organic phase was washed with 10% NaHCO$_3$ (10 mL×3) and dried with MgSO$_4$. The organic phase was removed under vacuum and flashed on silica (hexane:ethyl acetate 6:4) giving 111 mg (41.5%) of product. NMR revealed impurities of toluene-4-sulfonylchloride in product. Further purification was needed to remove 4-sulfonylchlodride. Using n-hexane:EtOAc (8:2) better separation was achieved on a silica flash column and the 4-sulfonylchloride was removed. Yield: 64 mg (22%). The product was analyzed by HPLC (column:Phenomenex Luna 3µ C18 (2), 4.6×50 mm, detection: 214 nm, gradient:20%-80% B over 10 min where A=H$_2$O/0.1% TFA and B=acetonitrile/0.1% TFA, flow rate: 2 mL/min, Rt=2.70 min). The product was identified by electrospray mass spectrometry (ESI-MS)(MH$^+$ calculated 373.16; found 373.9) Further confirmation was carried out by NMR analysis.

Example 2

Preparation of O-(4-fluoro-butyl)-(N-methyl-N-Boc-hydroxylamine) as cold standard Compound 2

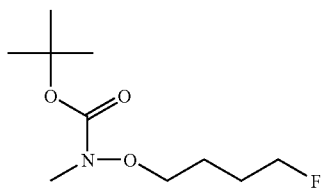

KF (4.64 mg, 0.080 mmol) and kryptofix (30.1 mg, 0.080 mmol) was dissolved in dry acetonitrile (0.75 mL). The mixture was stirred for 5 min after which compound 1 (15 mg, 0.040 mmol) dissolved in dry acetonitrile (0.250 mL) was added under argon. The mixture was heated at 60° C. for 1 hour. After one hour TLC showed that the reaction was completed. The solvent was evaporated and the residue was flashed on silicagel hexane/EtOAc (1:1) affording 4.5 mg (51%). The product was analyzed by HPLC (column:Phenomenex Luna 3µ C18 (2), 4.6×50 mm, detection: 214 nm, gradient:20%-70% B over 10 min where A=H$_2$O/0.1% TFA and B=acetonitrile/0.1% TFA, flow rate: 2 mL/min, Rt=2.70 min). The product was identified by electrospray mass spectrometry (ESI-MS)(MH$^+$ calculated 221.14; found 221.7). Structure confirmed with NMR.

Example 3

Radiosynthesis of $^{18}$F-compound 2 and conjugation to 2-bromo acetophenone

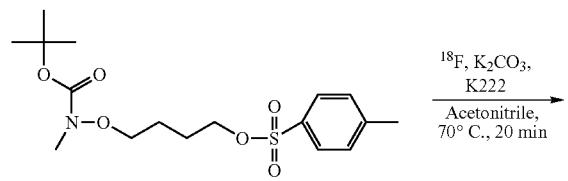

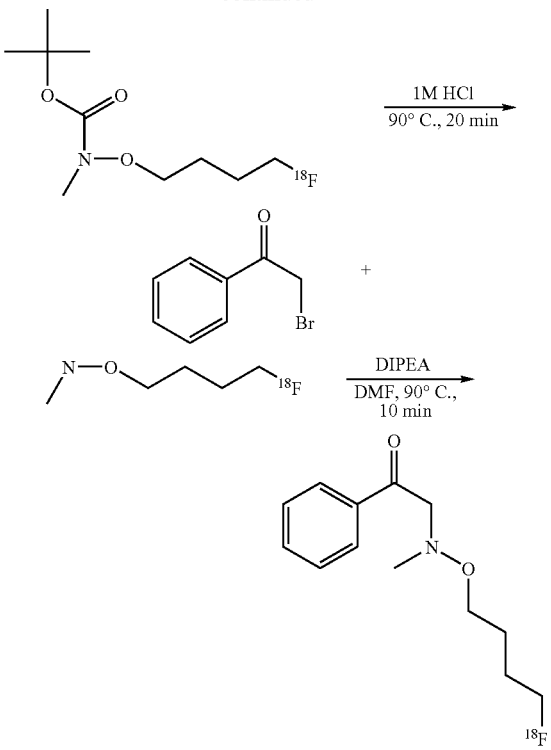

Radio synthesis was performed on SynChrom R & D module from Raytest. $^{18}$F-fluoride (up to 1 GBq) was azeotropically dried in the presence of Krytptofix 222 (39.1 mg in 1 mL acetonitrile) and potassium carbonate (65.7 mg in 1 mL water) by heating under N$_2$ to 90° for 9 minutes. During this time 2×1 mL acetonitrile were added and evaporated. After cooling to <40°, a solution of toluene-4-sulfonic acid 4-(N-Methyl-N-Boc-aminooxy)-butyl ester (compound 1) (3 mg in 1 mL acetonitrile) was added. The reaction vessel was heated to 70° C. for 20 minutes to effect labelling. The crude reaction mixture was injected to HPLC at 214 nm, with an isocratic flow using 60/40 CH$_3$CN/H$_2$O. Chromatogram showed good yields of the labelled compound about 86% RCP co-eluting with cold standard. The crude reaction mixture was eluted through a Sep-Pak aluminium column using 2 mL of ACN to remove free fluoride, the activity of the free fluoride was measured (less than 15% contributed by free fluoride). The "purified" mixture was reanalysed on HPLC, to see free fluoride is removed. 1 mL (100 MBq) of the purified product was hydrolysed in 1 mL 1 M HCl for 20 minutes at 90° C., to remove the BOC-protecting group, giving 100% of the unprotected F-18 radiolabelled compound. 1 mL of the hydrolysed product was diluted with 10 mL of milli-Q water and the pH was adjusted to pH 11-12 and eluted through a pre-conditioned SEP-PAK C-18 column. The activity on the column was measured to be 30.1 MBq. The column was eluted with 2 mL DMF into a reaction vial giving 2 mL with 23 MBq. 6 mg bromo-acetophenone was added with 10 µL diisopropyl ethyl amine and heated at 90° C. for 10 minutes. The reaction mixture was analyzed by HPLC showing evidence of conjugate formation by a new peak eluting at 5.46 minutes with a greater area (57%) than the peak corresponding to the "free" precursor. HPLC (column: Xterra (waters) 5µ C18 4.6×250 mm, detection: 250 and 214 nm, NaI detector Gradient: Isocratic; 40% A=H$_2$O and 60% C=acetonitrile flow rate: 1 mL/min).

Example 4

Preparation of Toluene-4-sulfonic acid 2-[2-(N-methyl-N-BOC-aminooxy)-ethoxy]-ethyl ester Compound 1

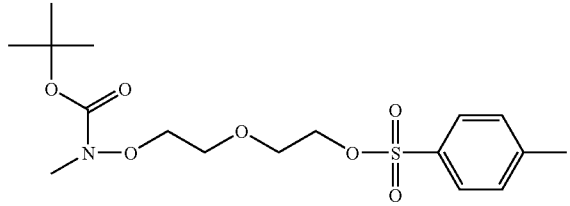

(a) N-Boc-N-methylhydroxylamine

N-methyl-hydroxylamine (4.2 g, 0.05 mol) was dissolved in a 50% aqueous tetrahydrofuran (THF) (20 ml) and cooled on ice while stirring. Potassium carbonate (3.6 g, 0.0275 mol) was added to the ice-cooled solution followed by di-tert-butyl dicarbonate (12 g, 0.055 mol) dissolved in 15 ml THF. The mixture was stirred at 0° C. for 2 hours and at room temperature for 2 hours. The THF was removed under reduced pressure and the residue was dissolved in DCM. The solution was washed two times with water, dried (MgSO$_4$), and concentrated giving a pink low viscous oil of 6.47 g (88%). The product was identified by electrospray mass spectrometry (ESI-MS)(MH$^+$ calculated 147.09; found 147.6) and NMR. The product was used in without further purification.

(b) toluene-4-sulfonic acid 2-(2-hydroxy-ethoxy)ethyl ester

To a solution of diethylene glycol (22 g, 207.5 mmol) in CH2Cl2 (100 ml) was added triethylamine (10.5 g, 103.75 mmol). 9.89 (51.8 mmol) Toluene-4-sulfonyl chloride was added in one portion. The solution was stirred at room temperature for 1 hour. TLC was performed in 5% MeOH in DCM. After ½ hour a TLC showed formation of product. After 1 hour and 15 minutes the reaction mixture was washed with 0.1 M KHSO3 and 5% NaHCO3. The organic phase was dried with Na2SO3 and evaporated under reduced pressure. The crude reaction mixture was trapped on silica and purified by flash chromatography on a CombiFlash companion instrument (330 g column) using Hexane/EtOAc 50/50. Structure confirmed NMR.

(c) 4-toluene-sulfonic acid 2-[2-(tert-butyl-diphenyl-silanyloxy)-ethoxy]-ethyl ester To a solution toluene-4-sulfonic acid 2-(2-hydroxy-ethoxy)ethyl ester (b) (7.622 g, 29.28 mmol) in CH2Cl2 (30 ml) containing i-Pr2-Net (6 mL, 1.2 Eq) was added t-BDPS-iCl (9 ml, 1.2 eq, 35.136 mmol) and a catalytic amount of DMAP under argon atmosphere. The solution was stirred at room temperature for 2 days. TLC suggested a complete reaction. The crude reaction mixture was diluted with 100 mL DCM and washed with 2*100 mL water and 100 mL brine. The organic phase was dried using MgSO4 and evaporated off under vacuum and purified by flash chromatograph on Companion Combiflash (120 g column) using a gradient (EtOAC/Hexane) from 0% ethyl acetate to 50% over 30 minutes. Appearance clear viscous oil. Structure confirmed by NMR.

(d) O-{2-[2-(tert-Butyl-diphenyl-silanyloxy)-ethoxy]-ethyl}-N-methyl-N-BOC-hydroxylamine In a oven dried flask (50 mL) was added NaH (60% disepersion in mineral oil) 481 mg (12.03 mmol) under argon. The dispersion was washed 3 times with pentane to remove the mineral oil. To the pure NaH was added 5 mL THF (dry). N-BOC-N-methyl hydroxyl amine (a) 1.53 mg (10.43 mmol) in 5 mL THF was added slowly. The reaction mixture was left for ½ an hour until no more gas production could be seen. The solution was put on ice-bath and stirred for ½ an hour after which 4 g (8.02 mmol) of 4-toluene-sulfonic acid 2-[2-(tert-butyl-diphenyl-silanyloxy)-ethoxy]-ethyl ester (c) was added dropwise. The solution was left on ice-bath for ½ an hour and then stirred over-night at RT. The solvents were removed under reduced pressure, and the residue was dissolved in EtOAc (200 mL) and poured into a separatory funnel. The organic layer was washed with 0.1 M NaOH (5×50 mL), H2O (50 ml), 0.1 m KHSO4, and brine (50 ml) and the dried with MgSO4. After removal of the solvent, the residue was purified using flash chromatography on a Companion Combiflash using a gradient of methanol in DCM (methanol: 0-20% over 19 minutes). Structure confirmed by NMR.

(e) 2-[2-(N-Methyl-N-BOC-aminooxy)-ethoxy]-ethanol

TBAF (6.78 mL, 6.78 mmol) was added to O-{2-[2-(tert-Butyl-diphenyl-silanyloxy)-ethoxy]-ethyl}-N-methyl-N-BOC-hydroxylamine (d) (3 g, 6.33 mmol) dissolved in dry THF (15 mL). The reaction was stirred over night. The THF was evaporated off and the residue was dissolved in DCM and washed with NH4Cl (saturated) (40 mL), water and brine. The organic phase was dried (MgSO4) and evaporated off. The residue was purified using flash chromatography on a Companion Combiflash 40 g column (Gradient MeOH 0-5% over 20 minutes in DCM. Structure confirmed by NMR.

(f) Toluene-4-sulfonic acid 2-[2-(N-methyl-N-BOC-aminooxy)-ethoxy]-ethyl ester To a stirred solution of 2-[2-(N-Methyl-N-BOC-aminooxy)-ethoxy]ethanol (e) 1 g (4.25 mmol) in dry DCM (15 mL) was added triethylamine (910 mg, 1254 μL, 9 mmol) and toluene-4-sulfonyl chloride (1620 mg, 8.5 mmol) in 15 mL DCM. The reaction mixture was stirred under argon overnight. TLC revealed a complete reaction (Hexane/Ethylacetate 6:4). The reaction mixture was diluted with 50 mL DCM and the organic phase was washed with NaHCO3 5%, brine and water. The organic phase was dried over MgSO4, filtered and evaporated off under reduced pressure. The product was purified using a Companion combiflash (40 g column) with a gradient of Hexane/Ethylacetate. 10-65% ethyl acetate in Hexane over 20 minutes. Structure confirmed by NMR.

Example 5

Preparation of O-[2-(2-Fluoro-ethoxyl)-ethyl]-N-methyl-N-BOC-hydroxylamine

Compound 2

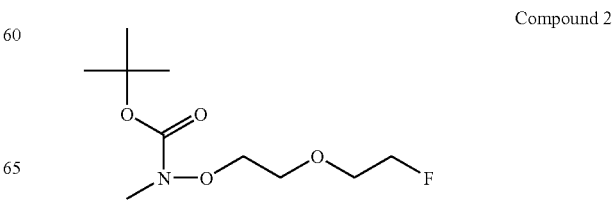

KF (58 mg, 1 mmol) and kryptofix (376 mg, 1 mmol) was dissolved in dry acetonitrile (2 mL). The mixture was stirred for 5 min after which compound 1 (200 mg, 0.51 mmol) dissolved in dry acetonitrile (0.250 mL) was added under argon. The mixture was heated at 80° C. for 1 hour. After one hour TLC revealed a complete reaction. The organic phase was evaporated of using reduced pressure, redissolved in DCM, and trapped on silicagel. The substance was purified using flash chromatography on silica gel hexane/Ethylacetete 1:1.

Yield: 83 mg (0.35 mmol). Structure confirmed with NMR.

Example 6

Preparation of Maleimido-Propionyl-Lys-Gly-Phe-Gly-Lys-OH

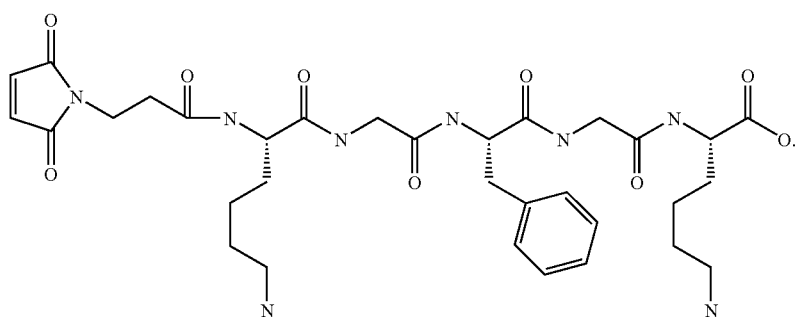

The model penta-peptide Lys-Gly-Phe-Gly-Lys-OH was assembled on a fully automated peptide synthesizer (ABI 433A synthesis machine) with Fmoc-Lys(Boc)-Sasrin resin (0.1 mmol) using the slowmoc Single Couple procedure with HBTU activation. The maleimdo-propionylic acid was coupled manually using 3-(maleimido)propionic acid N-hydroxysuccinimide ester (0.52 mmol). Simultaneous removal of the peptide from the resin and deprotection of side-chain protecting groups were carried out in trifluoroacetic acid containing triisopropylsilane and water 95:2.5:2.5 v/v/v). After filtration, the solution was concentrated under reduced pressure and the residue was washed with diethyl ether. The crude product was purified by reversed-phase preparative chromatography (Phenomenex Luna C18(2) column, 250*50 mm, 10 μm; gradient 0-30% solvent B over 60 min; flow rate 50 mL/minute), affording 66 mg (95%) of pure compound. The product was analyzed by LC-MS [Phenomenex Luna C18-(2), 50*2.0 mm, 5 μm; gradient 0-30% solvent B over 5 min; flow rate 0.6 mL/min; $t_R$=2.86 min], m/z=687.6 (M+H)$^+$, calc m/z=687.3 (M+H)$^+$.

Compound 3

Example 7

Radiosynthesis of $^{18}$F-Compound 2 and Conjugation to Compound 3

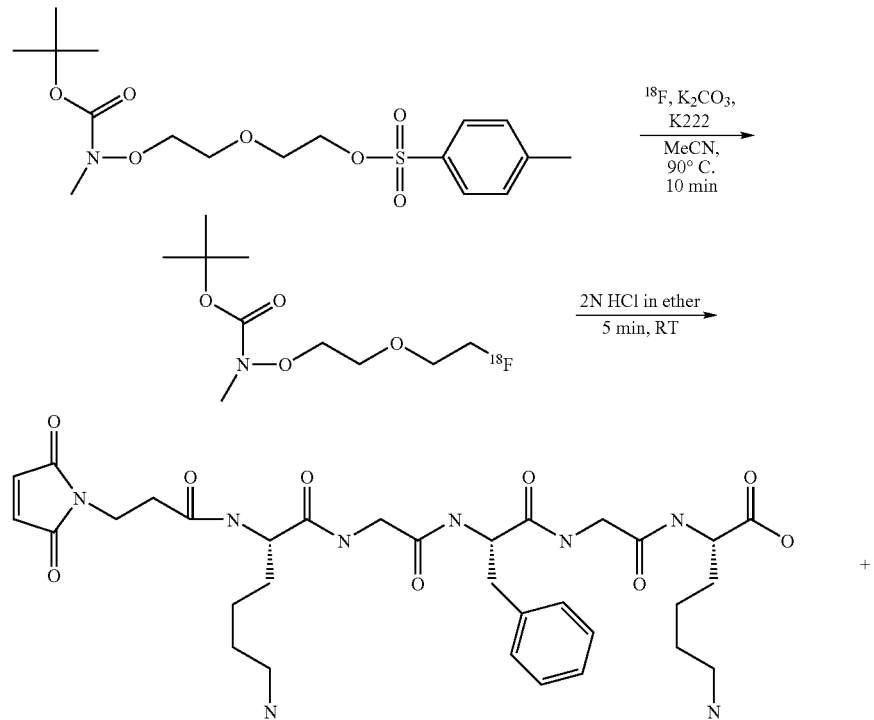

-continued

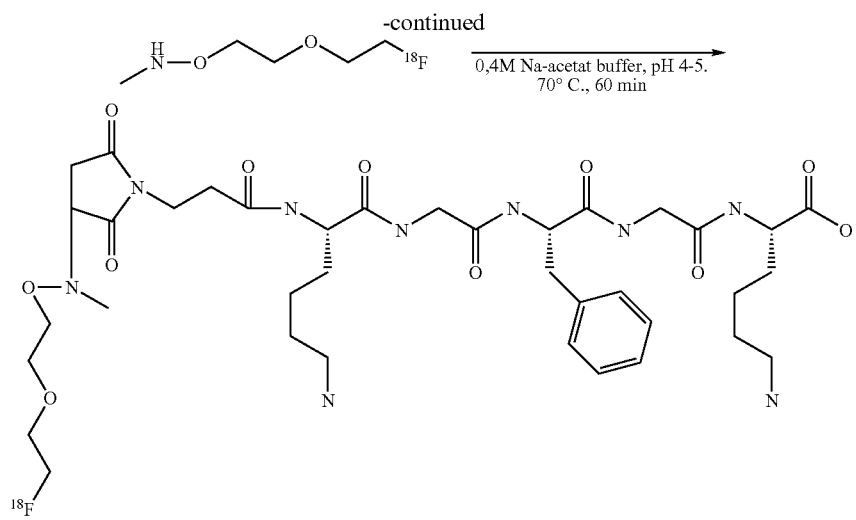

Radio synthesis was performed on a TracerLab FxFn module from GE Healtcare. $^{18}$F-fluoride (up to 350 MBq) was azeotropically dried in the presence of Krytptofix 222 (39.1 mg in 1 mL acetonitrile) and potassium carbonate (65.7 mg in 1 mL water) by heating under $N_2$ to 100° for 9 minutes. During this time 2×0.7 mL acetonitrile were added and evaporated. After cooling to <50°, a solution of toluene Toluene-4-sulfonic acid 2-[2-(N-methyl-N-BOC-aminooxy)-ethoxy]-ethyl ester (compound 1) (5 mg in 1 mL dry acetonitrile) was added. The reaction vessel was heated to 90° C. for 10 minutes to effect labelling. The crude reaction mixture was diluted with 5 mL water. A sample for TLC and 50 μL was injected to HPLC (Phenomenex gemine 150 mm*4.60 C18 5 μm) at 214 nm, 254 nm and gamme-detector with an gradient flow using solvent B 20-80% over 15 min. TLC (1:1 ethylacetate/hexane) gave good yields of the labelled compound≈70% (n=3). Compound co-eluted with cold reference standard. The crude reaction mixture was further diluted with 4 mL water and passed through an Oasis HLB Sep-Pak cartridge (preconditioned 5 mL MeCN and 10 mL $H_2O$). The Oasis cartridge was washed with 50 mL 25% methanol in water solution and the purified compound was eluted off using 1.5 mL MeCN. 0.3 mL 2N HCl in ether was added to the MeCN eluate and stirred for 5 minutes at RT to remove the BOC-group quantitatively, after which the organic phase was evaporated of at 65° C. under $N_2$-flow and reduced pressure for 3 minutes and another 3 minutes after adding 1 mL of MeCN. 5 mg of compound 3 in 0.8 mL 0.4M Na-acetate buffer pH 5 was added to the dried mixture and the reaction was heated to 70° C. for 60 min to effect conjugation. Sample was taken out at 0 min and 60 min.

The reaction mixture was analyzed by HPLC showing evidence of the formation of the conjugate to compound 3 by a new peak co-eluting with the F19-reference standard at 11 min with an area (74%) (FIG. 1). HPLC: Phenomenex gemine 150 mm*4.60 C18 5 μm, Gradient, solvent B 0-40% over 10 minutes and solvent B 40% 10-15 min.

Example 8

Preparation of
4-(2-nitrovinyl)benzoyl-Lys-Gly-Phe-Gly-Lys-OH

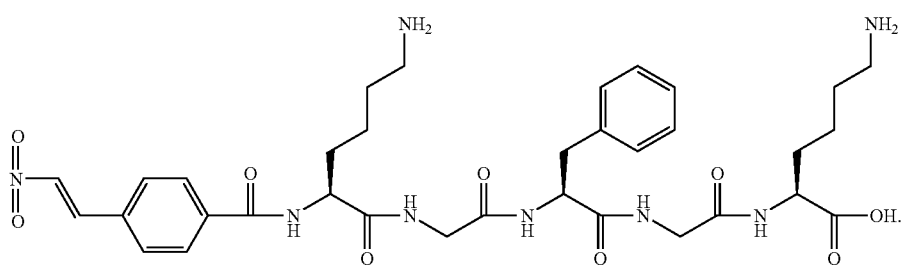

Compound 6

The model penta-peptide Lys-Gly-Phe-Gly-Lys-OH was assembled as described in example 6. 58 mg (0.3 mmol) trans-β-nitrostyrene and 156.5 mg (0.3 mmol) PyAOP was added to resin (0.2 mmol) in neat DMF after which 102 μL (0.6 mmol) DIPEA was added and the reaction was left for one hour. Simultaneous removal of the peptide from the resin and deprotection of side-chain protecting groups were carried out in trifluoroacetic acid containing triisopropylsilane and water 95:2.5:2.5 v/v/v). After filtration, the solution was concentrated under reduced pressure and the residue was washed with diethyl ether. The crude product was purified by reversed-phase preparative chromatography (Phenomenex Luna C18(2) column, 250*50 mm, 10 μm; gradient 0-40% solvent B over 60 min; flow rate 50 mL/minute), affording 101 mg (70%) of pure compound. The product was analyzed by LC-MS [Phenomenex Luna C18-(2), 50*2.0 mm, 5 μm; gradient 0-30% solvent B over 5 min; flow rate 0.6 mL/min; $t_R$=4.10 min], m/z=711.3 (M+H)$^+$, calc m/z=711.3 (M+H)$^+$.

Example 9

Conjugation of $^{18}$F-Compound 4 to Compound 6

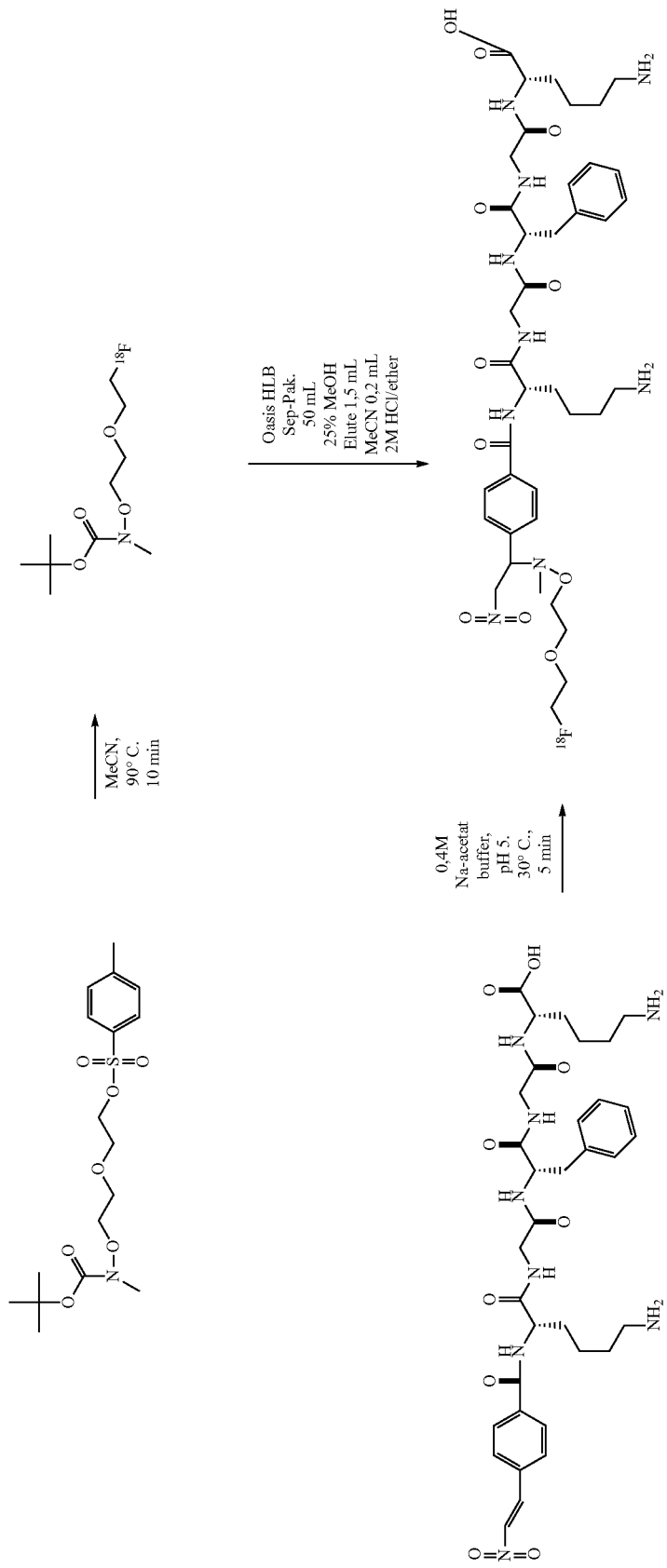

Radio synthesis and purification of compound $^{18}$F-compound 4 was performed as described as above in example 7. 0.2 mL 2N HCl in ether was added to the MeCN eluate containing $^{18}$F compound 4 and stirred for 5 minutes at RT to remove the BOC-group quantitatively, after which the organic phase was evaporated of at 65° C. under N$_2$-flow and reduced pressure for 3 minutes and another 3 minutes after adding 1 mL of MeCN.

Figure 2:
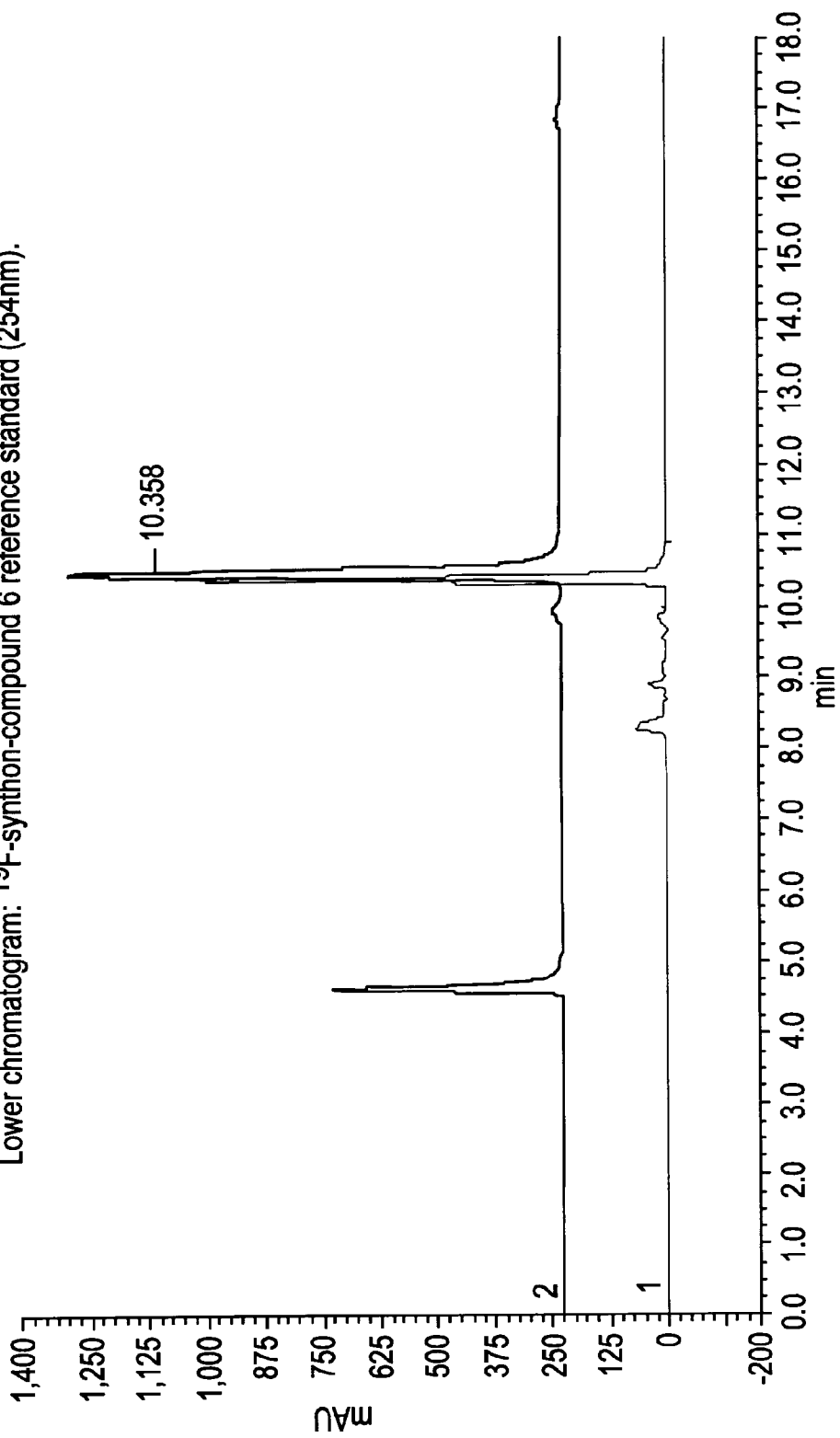
FIG. 2 shows HPLC chromatogram of $^{18}$F-conjugate of compound 6. Above chromatogram: Left peak unreacted $^{18}$F-synthon; right peak $^{18}$F-synthon-compound 6 conjugate. Lower chromatogram: $^{19}$F-synthon-compound 6 reference standard (254 nm).

5 mg of compound 6 in 0.8 mL 0.4M Na-acetate buffer pH 5 was added to the dried mixture and the reaction was heated at 30° C. for 5 min. The reaction mixture was analyzed by HPLC showing evidence of the formation of the conjugate by a new peak co-eluting with the $^{19}$F-reference standard at 10.4 min with an area (72%) (FIG. 2). HPLC: Phenomenex gemine 150 mm*4.60 C18 5 μm, Gradient, solvent B 0-40% over 10 minutes and solvent B 40% 10-15 min.

Example 10

Preparation of Maleimido-Propionyl-RDG-Peptide 50 mg (0.04 mmol) of the peptide NC100717 was dissolved in 1 mL DMF in 5 mL vessel. 21.3 mg (0.1 mmol) 3-(maleimido)propionic acid N-hydroxysuccinimide ester was dissolved in 1 mL DMF together with DIPEA 13.6 μl (0.08 mmol) and added to the peptide solution. The reaction was stirred for 1 hour at RT. The DMF was evaporated off. The crude product was purified by reversed-phase preparative chromatography (Phenomenex Luna C18(2) column, 250*50 mm, 10 μm; gradient 0-40% solvent B over 60 min; flow rate 50 mL/minute), affording 23 mg (40%) of pure compound. The product was analyzed by LC-MS [Phenomenex Luna C18-(2), 50*2.0 mm, 5 μm; gradient 5-40% solvent B over 5 min; flow rate 0.6 mL/min; $t_R$=2.74 min], m/z=1409.9 (M+H)$^+$, calc m/z=1409.5 (M+H)$^+$.

Example 11

Conjugation of $^{18}$F-Compound 4 to Compound 7

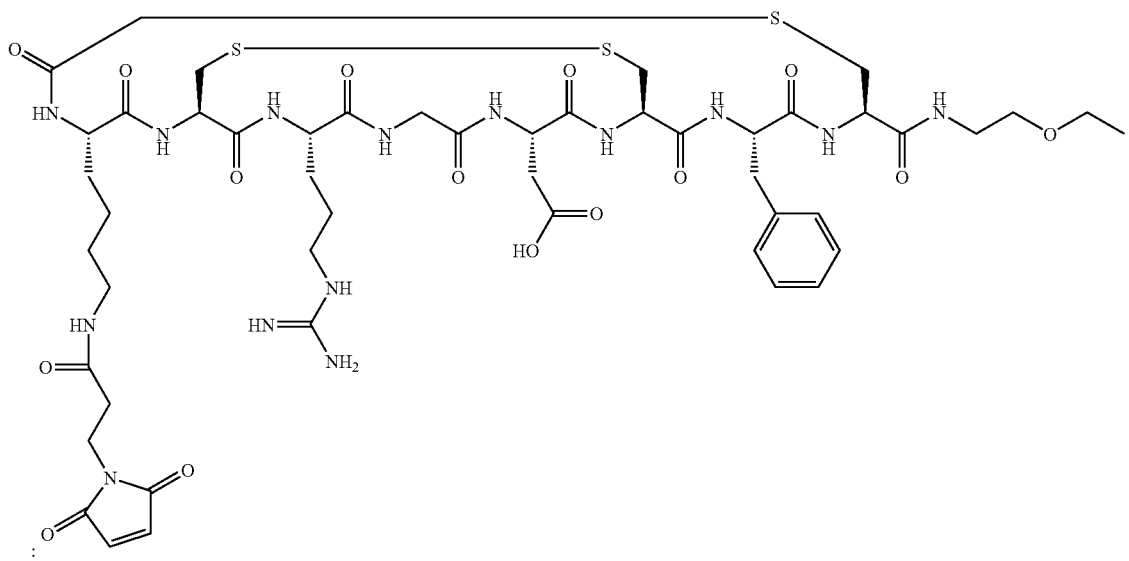

Compound 7

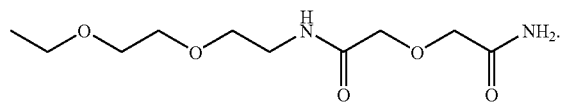

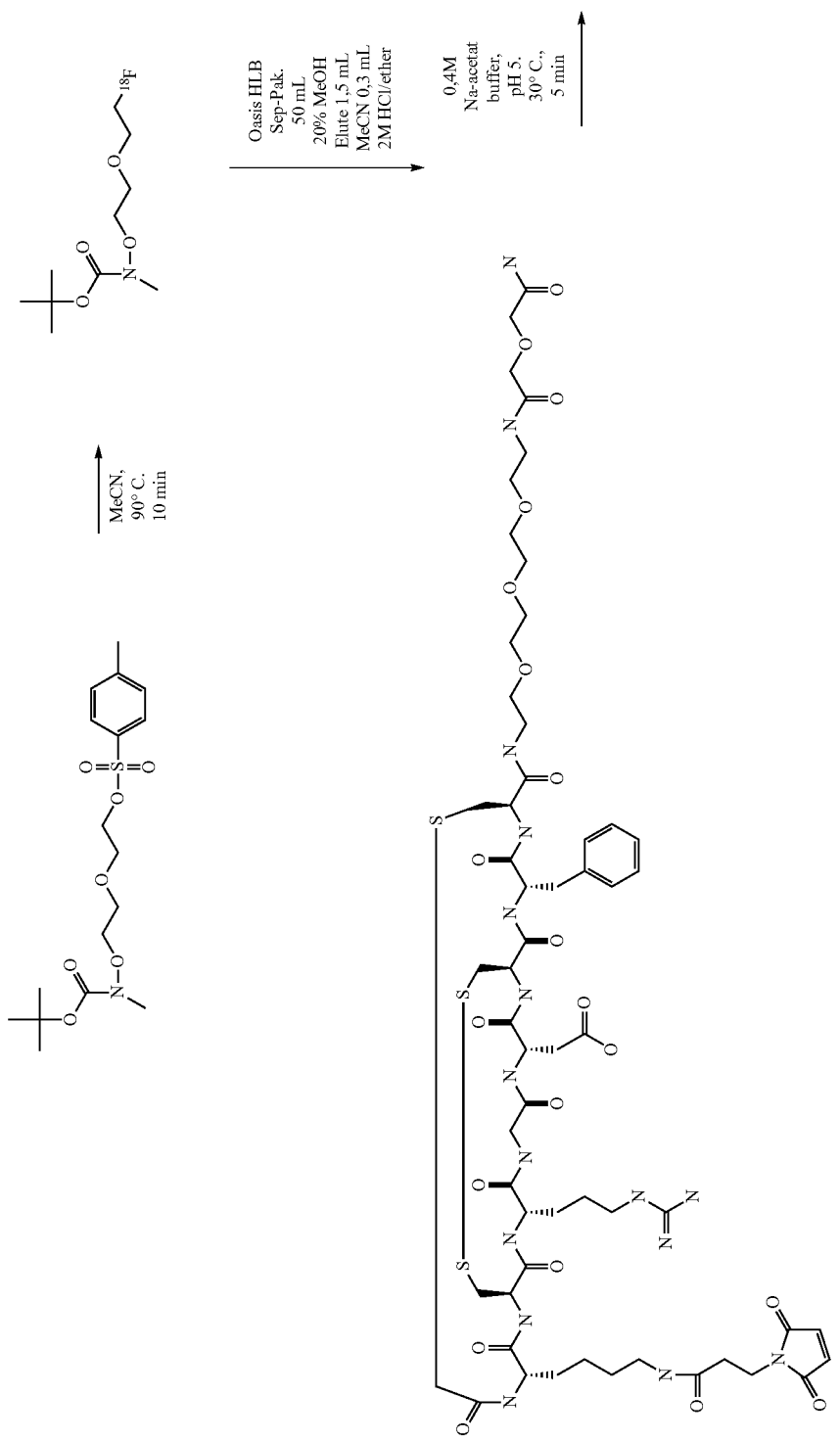

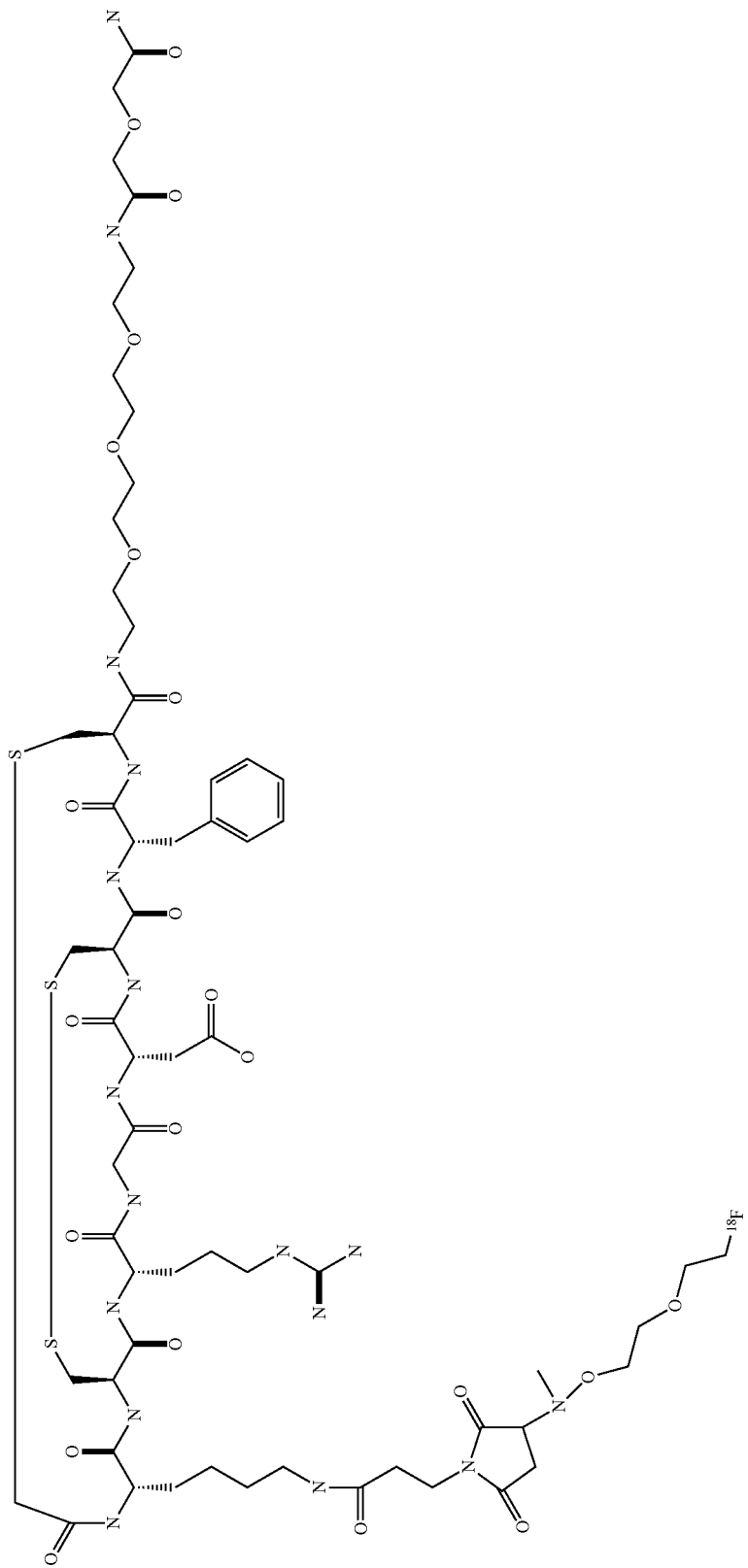

Figure 3:
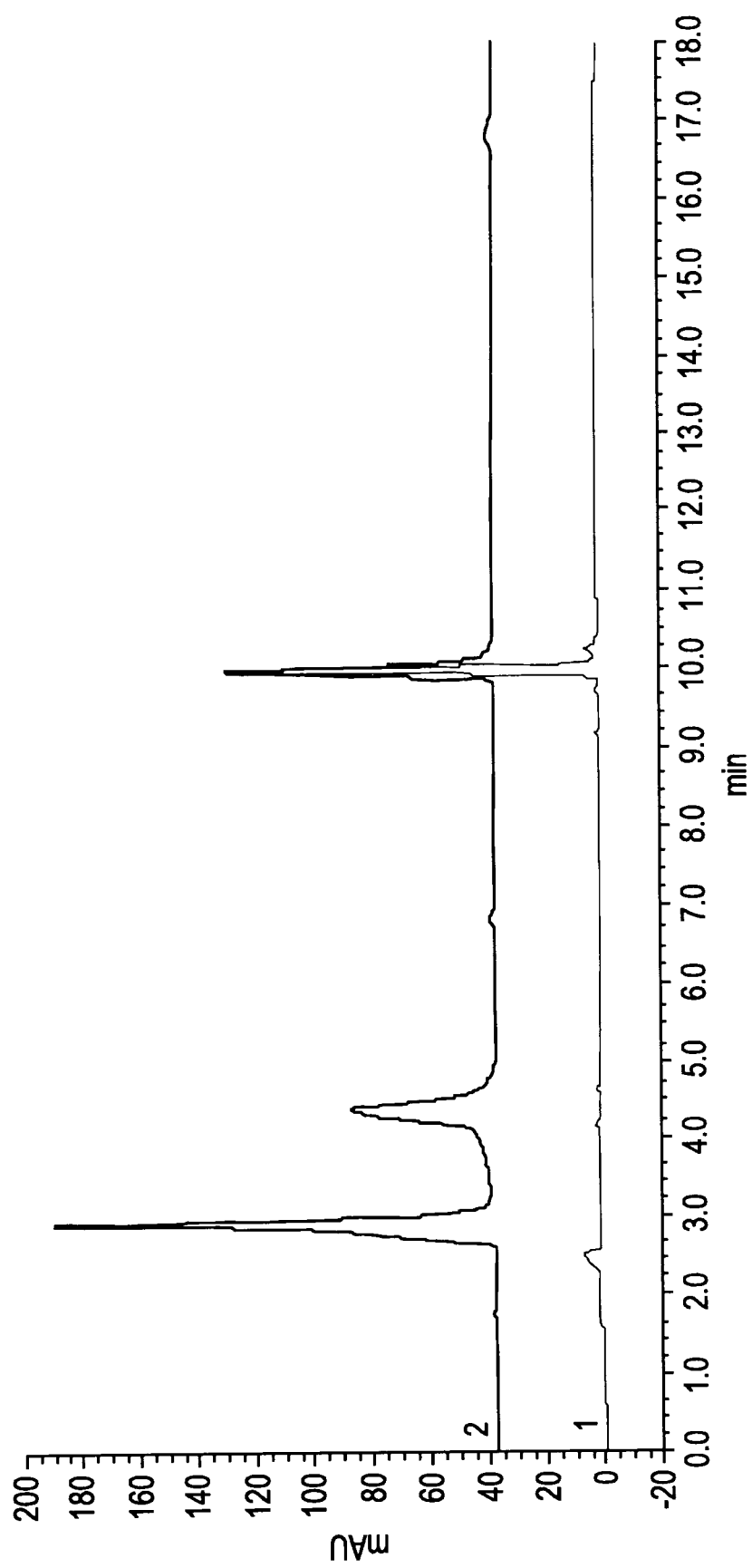
FIG. 3 shows HPLC chromatogram of $^{18}$F-conjugate of compound 7. Above chromatogram: Left peaks unreacted $^{18}$F-synthon; right peak $^{18}$F-synthon-compound 7 conjugate. Lower chromatogram: $^{19}$F-synthon-compound 7 reference standard (254 nm).

Radiosynthesis and purification of compound $^{18}$F-compound 4 was performed as described as above in example 7. 0.2 mL 2N HCl in ether was added to the MeCN eluate and stirred for 5 minutes at RT to remove the BOC-group quantitatively, after which the organic phase was evaporated of at 65° C. under $N_2$-flow and reduced pressure for 3 minutes and another 3 minutes after adding 1 mL of MeCN. 5.75 mg of compound 7 in 0.6 mL 0.4 M acetate-buffer pH 5+0.4 mL DMF was added to the dried residue. The peptide mix was heated to 70° C. sample was taken out after 45. The crude reaction mixture was analysed by radio-HPLC giving 24% incorporation of $^{18}$F-synthon into peptide after 45 min, $^{18}$F-compound co-eluted with its authentic standard. (FIG. 3). HPLC: Phenomenex gemine 150 mm*4.60 C18 5 µm, Gradient, solvent B 0-40% over 10 minutes and solvent B 40% 10-15 min.

Example 11

Preparation of Benzoyl-Trans-β-Nitrostyrene-RDG 40 mg (0.032 mmol) of the peptide NC100717 was dissolved in 2 mL DMF. Trans-β-nitrostyrene 12.3 mg (0.064 mmol) and PyaOP 25 mg (0.048 mmol) dissolved in 2 mL DMF and DIPEA 16 µL (0.096 mmol) was added. The mixture was pre-activated for 10 minutes after which it was added to the peptide (NC100717). After 15 minutes a LC-MS indicated a complete reaction, and the reaction mixture was quenched with MeCN/0.1% TFA (20 mL). The organic phase was removed under reduced pressure. The crude product was purified by reversed-phase preparative chromatography (Phenomenex Luna C18(2) column, 250*50 mm, 10 µm; gradient 5-45% solvent B over 60 min; flow rate 50 mL/minute), affording 12 mg (26%) of pure compound. The product was analyzed by LC-MS [Phenomenex Luna C18-(2), 50*2.0 mm, 5 µm; gradient 5-40% solvent B over 5 min; flow rate 0.6 mL/min; $t_R$=2.74 min], m/z=1433.6 (M+H)$^+$, calc m/z=1433.5 (M+H)$^+$.

Example 12

Conjugation of $^{18}$F-Compound 4 to Compound 8

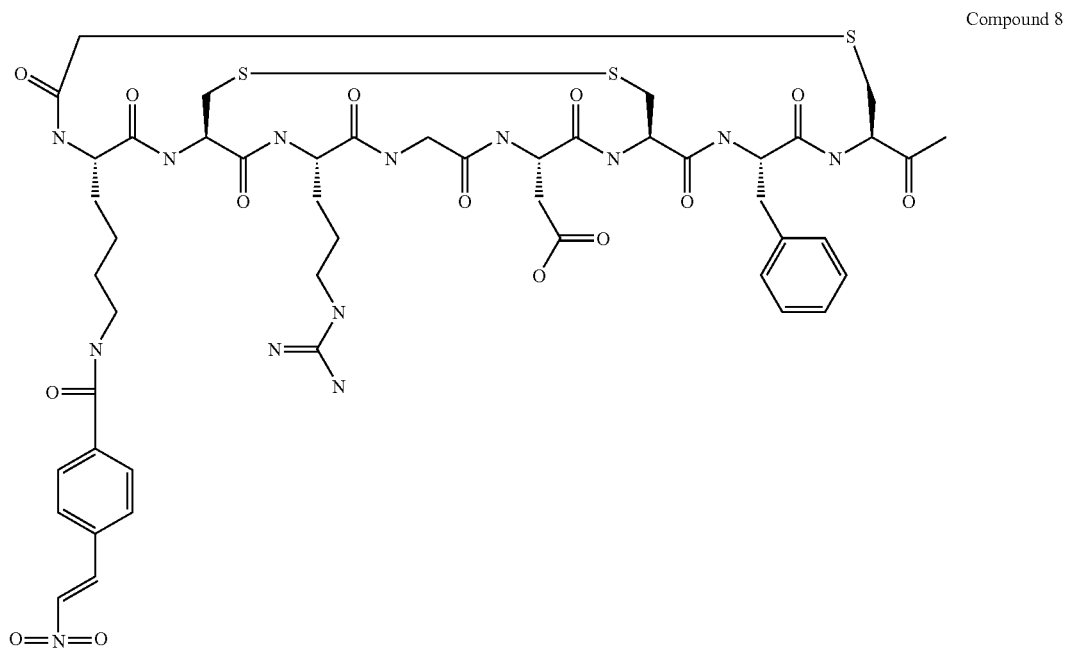

Compound 8

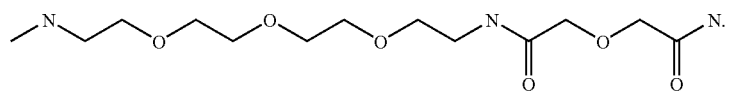

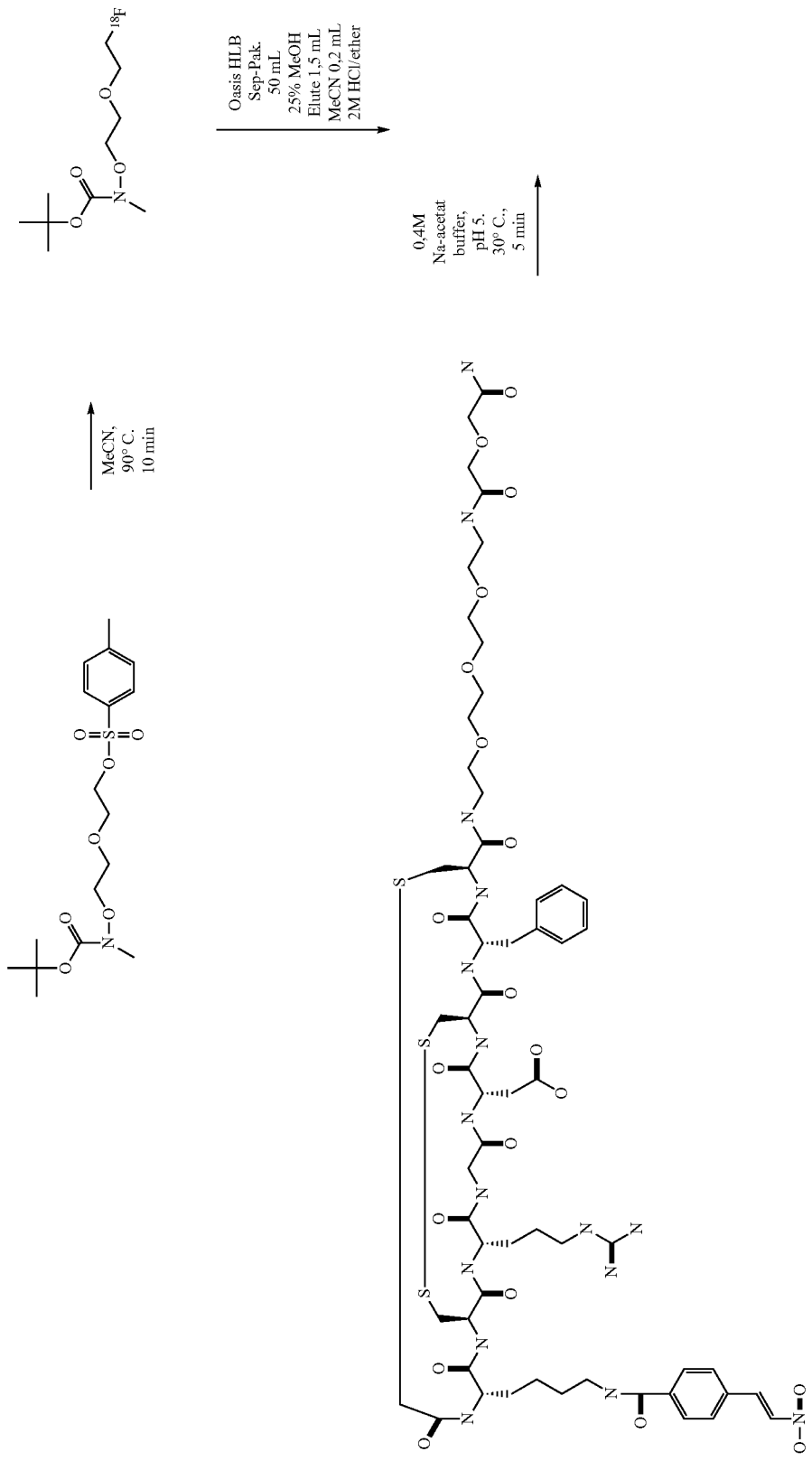

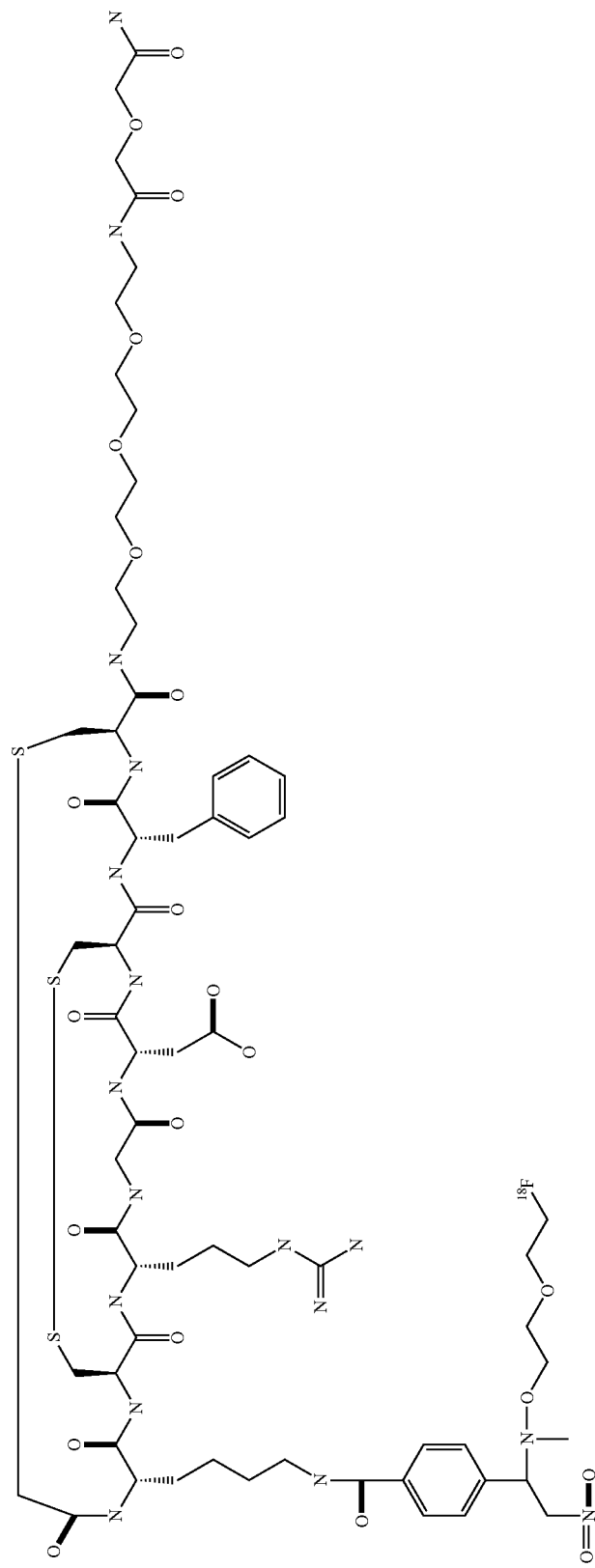

Figure 4:
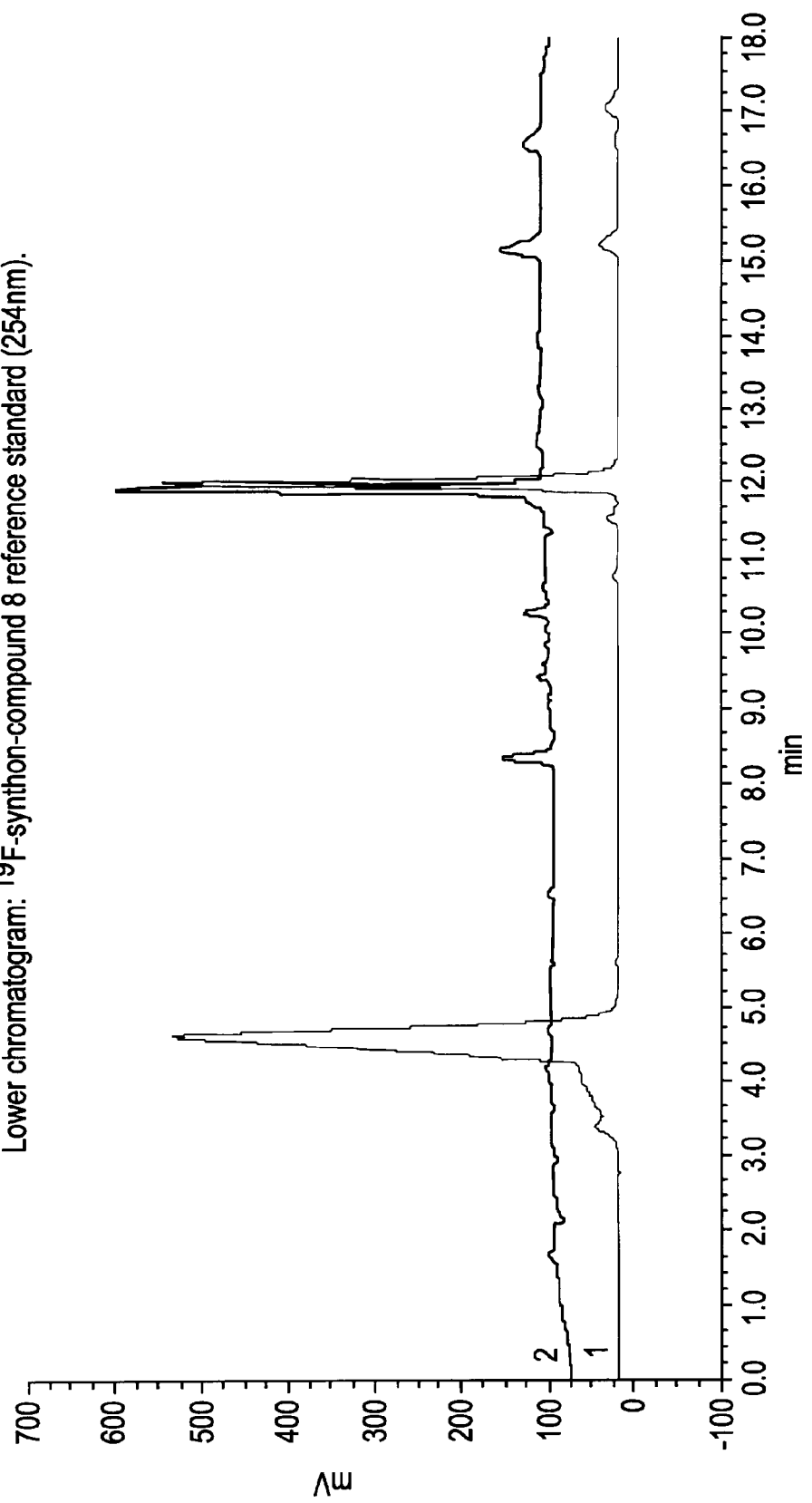
FIG. 4 shows HPLC chromatogram of $^{18}$F-conjugate of compound 8. Above chromatogram: Left peak: unreacted $^{18}$F-synthon; right peak $^{18}$F-synthon-compound 8 conjugate. Lower chromatogram: $^{19}$F-synthon-compound 8 reference standard (254 nm).
Figure 5:
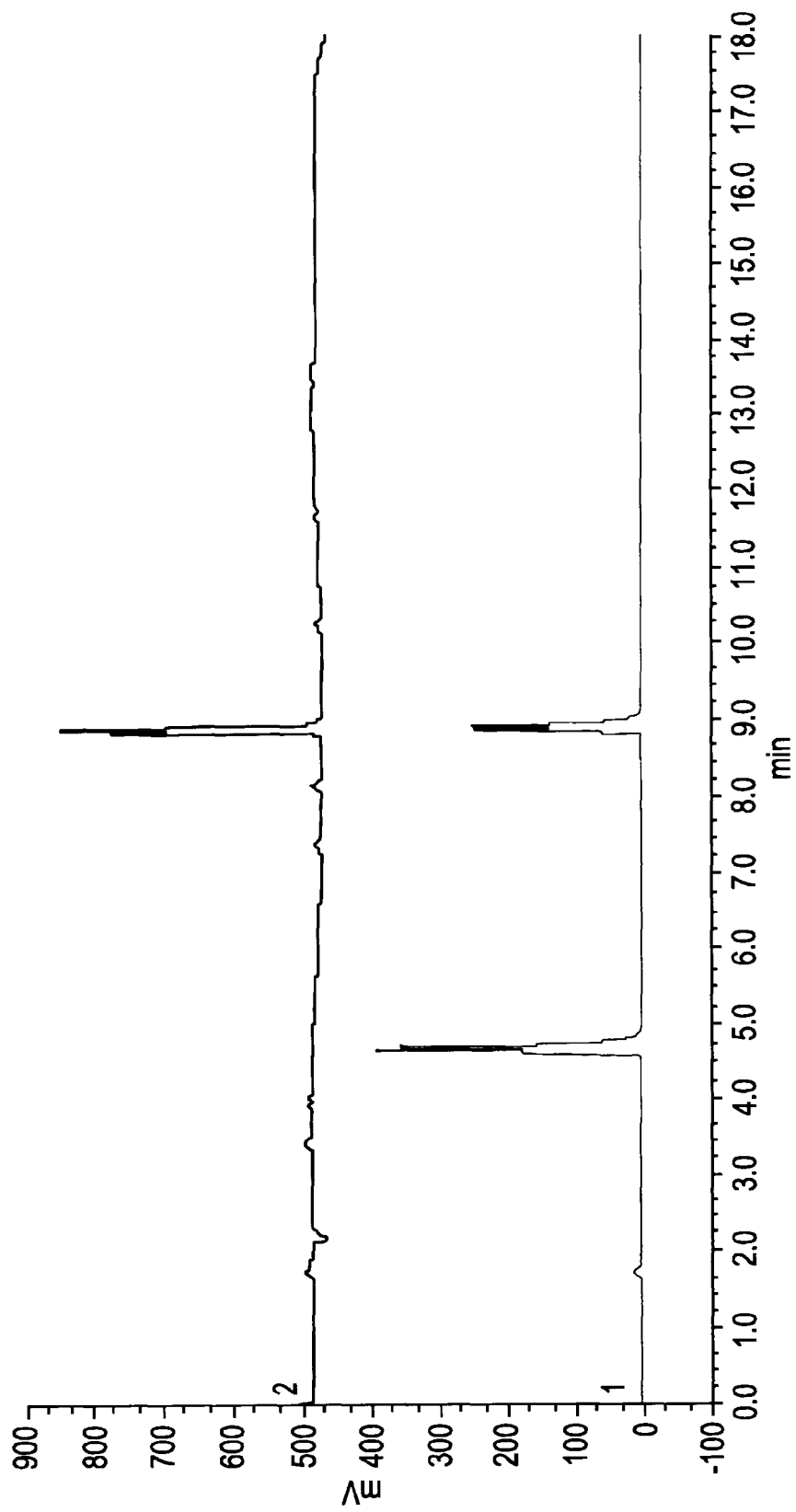
FIG. 5 shows HPLC chromatogram of $^{18}$F-conjugate of compound 11. Above chromatogram: $^{19}$F-synthon-compound 11 reference standard (254 nm). Lower chromatogram: Left peak: unreacted $^{18}$F-synthon; right peak $^{18}$F-synthon-compound 11 conjugate.

Radiosynthesis and purification of compound $^{18}$F-compound 4 was performed as described as above in example 7. 0.2 mL 2N HCl in ether was added to the MeCN eluate and stirred for 5 minutes at RT to remove the BOC-group quantitatively, after which the organic phase was evaporated of at 65° C. under $N_2$-flow and reduced pressure for 3 minutes and another 3 minutes after adding 1 mL of MeCN. Compound 8 (5 mg) in 0.8 mL 0.4 M acetate-buffer pH 5+0.4 mL DMF was added to the dried residue. The reaction was left for 5 minutes at 30° C. The crude reaction mixture was analysed by radio-HPLC giving 25% incorporation of $^{18}$F-synthon into peptide after 5 min, $^{18}$F-compound co-eluted with its authentic standard at 12 min. (FIG. 4). HPLC: Phenomenex gemine 150 mm*4.60 C18 5 μm, Gradient, solvent B 0-40% over 10 minutes and solvent B 40% 10-15 min.

Example 13

Synthesis of Ethenesulfonyl-Acetic Acid

Compound 9

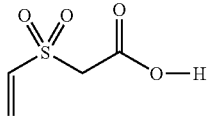

In a 250 mL 3-necked round-bottomed flask was dissolved 1.1 g (47.5 mmol, 1.2 eq) sodium in 25 mL absolute ethanol. After evolution of $H_2$ and disappearance of the sodium was complete, ethyl 2-mercaptoacetate (4.60 mL, 40.7 mmol, 1 eq) was added dropwise. The resulting mixture was stirred for 20 minutes after which 57 mL (57 mmol, 1.4 eq) vinyl bromide (1 M solution in THF) was added. The mixture was transferred to an autoclave and heated to 105° C. for 1 hour. The reaction mixture was left stirring for 4 hours. THF and EtOH were then evaporated in vacuo and the residue dissolved in water (120 mL) and extracted with diethyl ether (5×60 mL). The organic phase was dried over ($MgSO_4$) and XS solvent removed in vacuo. The crude material (2.9 g) was then dissolved in 10 mL glacial acetic acid and cooled to 0° C. Peracetic acid 36-40% (7.4 mL, 40 mmol) was added and the reaction mixture stirred for 30 min at 0° C. after which the temperature was allowed to rise to room temperature with continued stirring for a further 2 h. The solvent was again removed under vacuo and the crude product purified by flash chromatography on an automatic combiflash machine (20%-100% ethyl acetate in hexane over 10 minutes). NMR confirmed the structure to be the sulphoxide. All fractions were collected and oxidized further with peracetic acid (2 eq) in relation to sulphoxide (1.5 g, 9.2 mmol) until all starting material was gone. The crude product was used further without purification. Ethenesulfonyl-acetic acid ethyl ester was dissolved in 20 mL 0.1 M HCl and the mixture refluxed for 13 hours at 100° C. to yield ethenesulfonyl-acetic acid (1.2 g, 8 mmol). The structure was confirmed by NMR.

Preparation of Ethensulfonyl-Acetyl-Lys-Gly-Phe-Gly-Lys-OH

Compound 10

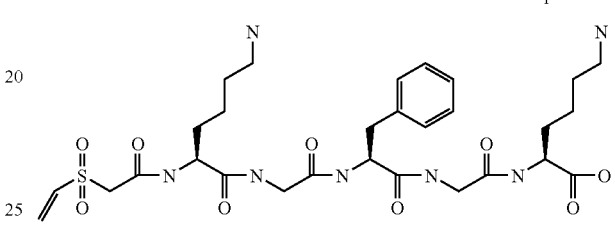

The model penta-peptide Lys-Gly-Phe-Gly-Lys-OH was assembled as described in example 6. 75 mg (0.5 mmol) ethenesulfonyl-acetic acid and 261 mg (0.5 mmol) PyAOP was added to peptide-bound resin (0.1 mmol) in neat DMF (5 mL) after which 171 μL (1 mmol) DIPEA was added and the reaction was left for two h. Simultaneous removal of the peptide from the resin and deprotection of side-chain protecting groups were carried out in trifluoroacetic acid containing triisopropylsilane and water 95:2.5:2.5 v/v/v). After filtration, the solution was concentrated under reduced pressure and the residue was washed with diethyl ether. The crude product was purified by reversed-phase preparative chromatography (Phenomenex Luna C18(2) column, 250*50 mm, 10 μm; gradient 0-30% solvent B over 60 min; flow rate 10 mL/minute), affording 51 mg (76%) of pure compound. The product was analyzed by LC-MS [Phenomenex Luna C18-(2), 50*2.0 mm, 5 μm; gradient 0-30% solvent B over 5 min; flow rate 0.6 mL/min; $t_R$=2.61 min], m/z=668.4 $(M+H)^+$, calc m/z=668.3 $(M+H)^+$.

Conjugation of [18]F-Compound 4 to Compound 10

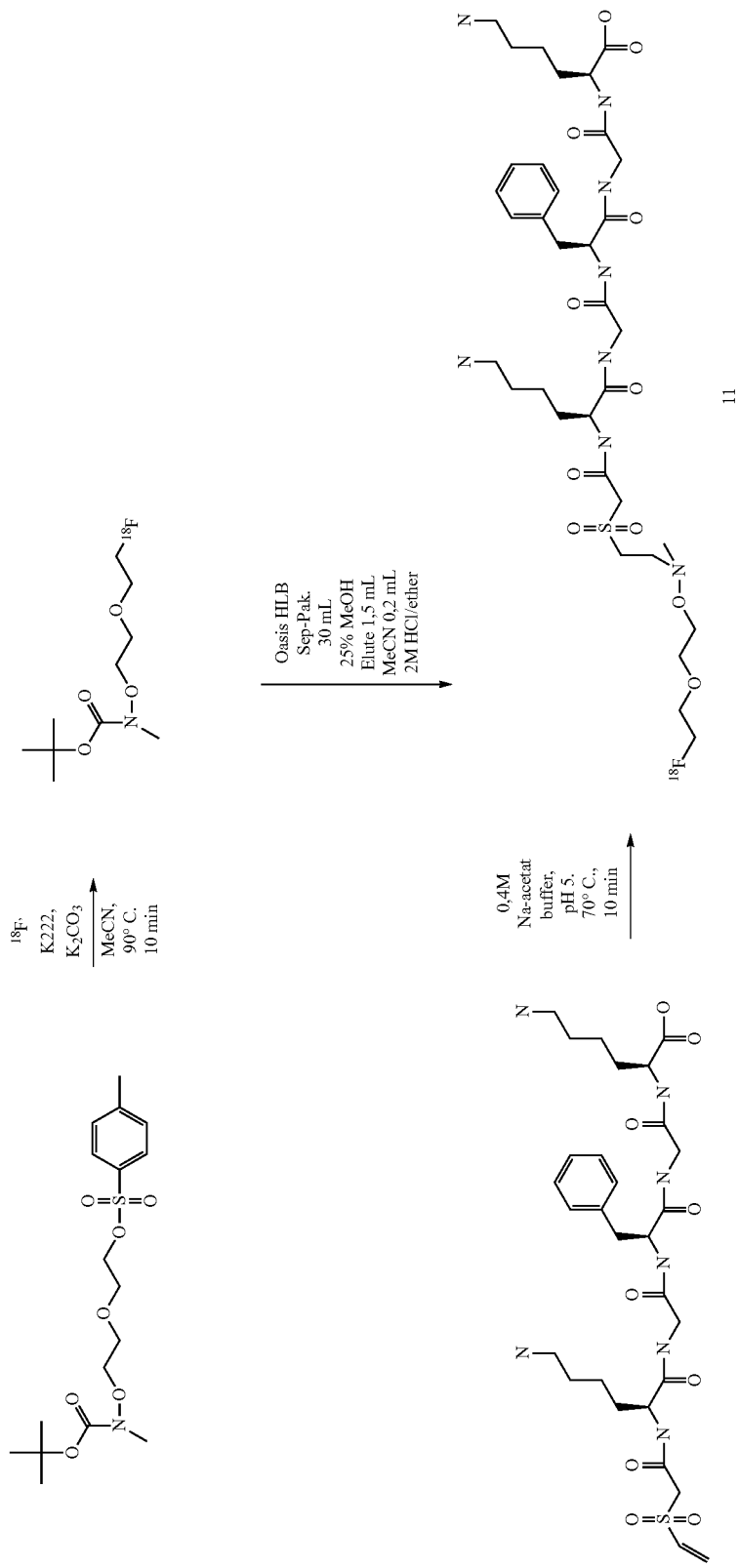

Radio synthesis was performed on a TracerLab FxFn module from GE Medical systems. $^{18}$F-fluoride (200 MBq) was azeotropically dried in the presence of 56 mg Kryptofix 222 ($K_{222}$: 4,7,13,16,21,24-hexaoxa-1,10-diazabicylo[8.8.8] hexacosane) and 10 mg $K_2CO_3$ dissolved in 215 μL water and 785 μL acetonitrile (total 0.8 mL) by heating under $N_2$-flow an vacuum at 100° for 9 minutes. During this time 2×0.8 mL acetonitrile were added and evaporated. After cooling to <50°, a solution of toluene Toluene-4-sulfonic acid 2-[2-(N-methyl-N-Boc-aminooxy)-ethoxy]-ethyl ester (compound 3) (3 mg in 1 mL dry MeCN) was added. The closed reaction vessel was heated to 90° C. for 10 minutes to effect labelling. The crude reaction mixture was diluted with 9 mL water and passed through an Oasis HLB Sep-Pak cartridge (Waters) (preconditioned 5 mL MeCN and 10 mL $H_2O$). The Oasis cartridge was washed with 50 mL 25% MeOH in water solution and the purified compound was eluted off using 1.5 mL MeCN. 2N HCl (0.2 mL) in ether was added to the MeCN eluate and mixture stirred for 5 minutes at RT to remove the Boc-group quantitatively. The organic phase was removed in vacuo at 65° C. under $N_2$-flow over 3 minutes followed by addition of 1 mL of MeCN with removal once again in vacuo for 3 minutes. 5 mg of compound 10 in 0.8 mL 0.4M Na-acetate buffer pH 5 was added to the dried mixture and the reaction was heated to 70° C. for 10 min to effect conjugation. The reaction mixture was analyzed by HPLC showing evidence of the formation of the conjugate (new peak co-eluting with the $^{19}$F-reference standard at 8.92 min, 40% yield) HPLC: Phenomenex gemine 150 mm*4.60 C18 5 μm, Gradient, solvent B 0-40% over 10 minutes and solvent B 40% 10-15 min.

What is claimed is:

1. A method for radiofluorination comprising reaction of a vector precursor of formula (I) with a compound of formula (IIb):

R1—[vector]  (I)

HN(CH$_3$)—OCH$_2$CH$_2$OCH$_2$CH$_2$$^{18}$F  (IIb)

to give a conjugate of formula (Va):

$^{18}$F-(Linker)-O—N(CH$_3$)—[vector]  (Va)

wherein
Linker=—CH$_2$CH$_2$OCH$_2$CH$_2$—
the vector is of formula (A):

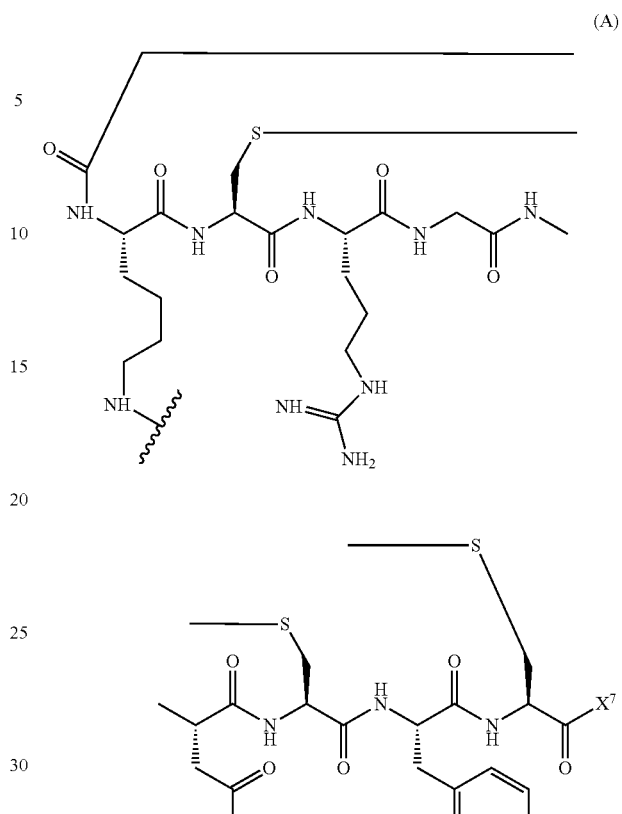

wherein $X^7$ is either —NH$_2$ or

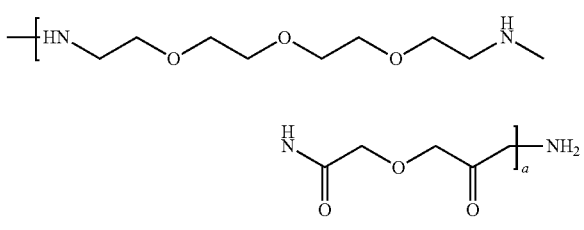

wherein a is an integer of from 1 to 10, and
R1 is of formula (Id) or (Ie):

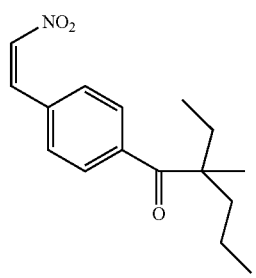

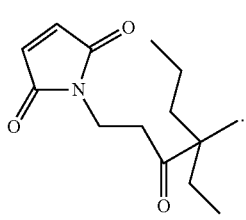

(Ie)

2. A method of generating an image of a human or animal body comprising administering a compound of Formula (Va) of claim 1 to said body and generating an image of at least a part of said body to which said compound has distributed using PET.

3. A method of monitoring the effect of treatment of a human or animal body with a drug to combat a condition associated with cancer, preferably angiogenesis, said method comprising administering to said body a compound of Formula (Va) of claim 1 and detecting the uptake of said compound by cell receptors said administration and detection optionally but preferably being effected before, during and after treatment with said drug.

4. The method of claim 1, where the compound of Formula IIb is generated from $^t$BuO(C=O)N(CH$_3$)—OCH$_2$CH$_2$OCH$_2$CH$_2$$^{18}$F.

* * * * *